United States Patent
Naudet et al.

(10) Patent No.: US 12,102,091 B2
(45) Date of Patent: Oct. 1, 2024

(54) CONTROL OF PLANT PESTS USING RNA MOLECULES

(71) Applicant: SYNGENTA CROP PROTECTION AG, Basel (CH)

(72) Inventors: Yann Naudet, Gent-Zwijnaarde (BE); Kaat Cappelle, Gent-Zwijnaarde (BE); Jennifer Diaz Gonzalez, Gent-Zwijnaarde (BE); Lies Degrave, Gent-Zwijnaarde (BE); Myriam Beghyn, Gent-Zwijnaarde (BE); Lien De Schrijver, Gent-Zwijnaarde (BE)

(73) Assignee: SYNGENTA CROP PROTECTION AG, Basel (CH)

( * ) Notice: Subject to any disclaimer, the term of this patent is extended or adjusted under 35 U.S.C. 154(b) by 551 days.

(21) Appl. No.: 17/275,460

(22) PCT Filed: Sep. 12, 2019

(86) PCT No.: PCT/US2019/050716
§ 371 (c)(1),
(2) Date: Mar. 11, 2021

(87) PCT Pub. No.: WO2020/056070
PCT Pub. Date: Mar. 19, 2020

(65) Prior Publication Data
US 2022/0408732 A1    Dec. 29, 2022

Related U.S. Application Data

(60) Provisional application No. 62/730,712, filed on Sep. 13, 2018.

(51) Int. Cl.
*A01N 63/60* (2020.01)
*C12N 15/113* (2010.01)
*A01P 7/04* (2006.01)

(52) U.S. Cl.
CPC ............ *A01N 63/60* (2020.01); *C12N 15/113* (2013.01); *A01P 7/04* (2021.08); *C12N 2310/14* (2013.01)

(58) Field of Classification Search
None
See application file for complete search history.

(56) References Cited

U.S. PATENT DOCUMENTS

| | | |
|---|---|---|
| 8,906,876 B2 | 12/2014 | Raemaekers et al. |
| 2012/0240288 A1 | 9/2012 | Ye et al. |
| 2015/0128303 A1 | 5/2015 | Raemaekers et al. |
| 2016/0230185 A1 | 8/2016 | Baum et al. |
| 2017/0121732 A1 | 5/2017 | Nibblet |

FOREIGN PATENT DOCUMENTS

| | | | |
|---|---|---|---|
| WO | 2007083193 A2 | 7/2007 | |
| WO | 2011153418 A2 | 12/2011 | |
| WO | 2016018887 A1 | 2/2016 | |
| WO | WO-2016105696 A1 * | 6/2016 | ............ A01N 57/16 |
| WO | 2017132330 A1 | 8/2017 | |

OTHER PUBLICATIONS

Fourgoux-Nicol et al. Plant Molecular Biology (1999), 40: 857-872.*
Thomas et al. Plant J. (2001), 25:417-425.*
Written Opinion of the International Authority and International Search Report for PCT Application No. PCT/US2019/050716 mailed Jan. 27, 2020.
Jason Lancaster et al., "De novo formation of an aggregation pheromone precursor by an isoprenyl diphosphate synthase-related terpene synthase in the harlequin bug", Proceedings of the National Academy of Sciences, Aug. 23, 2018, pp. 1-8, vol. 115, No. 37.
Kanakachari Mogilicherla et al: "Improving RNAi in the Brown Marmorated Stink Bug: Identification of target genes and reference genes for RT-qPCR", Scientific Reports, Feb. 27, 2018, pp. 1-9, vol. 8, No. 1.
Courtney Davis-Vogel et al: "Identification and comparison of key RNA interference machinery from western corn rootworm, fall armyworm, and southern green stink bug", PLOS One, Sep. 5, 2018, pp. 1-26, vol. 13, No. 9.
EPO; App. No. EP 19859213.1; Extended European Search Report mailed Sep. 23, 2022; pp. 1-21.
Bingsohn, L et al., Knockdown of genes in the Toll pathway reveals new lethal RNA interference targets for insect pest control, Insect Molecular Biology, vol. 26, No. 1, Nov. 15, 2016, pp. 92-102.
Fishilevich, Elaine et al., Use of chromatin remodeling ATPases as RNAi corn rootworm (*Diabrotica virgifera virgifera*) and Neotropical brown stink bug (*Euschistus heros*), Insects Biochemistry and Molecular Biology, vol. 71, Feb. 10, 2016, pp. 58-71.
Vallier, Agnes et al., RNAi in the cereal weevil *Sitophilus* spp: Systemic gene knockdown in the bacteriome tissue, BMV Biotechnology, vol. 9, No. 1, May 15, 2009, p. 44.
Zhao, Y.Y. et al., PsOr1, a potential target for RNA interference-based pest management, Insect Molecular Biology, vol. 20, No. 1, Sep. 21, 2010, pp. 97-104.
Partial Supplementary European Search Report for EP Application No. 19859213.1 dated May 25, 2022.

* cited by examiner

*Primary Examiner* — Medina A Ibrahim
(74) *Attorney, Agent, or Firm* — BakerHostetler; Toni-Junell Herbert

(57) ABSTRACT

Disclosed are double stranded RNA (dsRNA) molecules that are toxic to coleopteran and/or hemipteran insect pests. In particular, interfering RNA molecules capable of interfering with pest insect target genes and that are toxic to the target insect pest are provided. Further, methods of making and using the interfering RNA, for example in transgenic plants or as the active ingredient in an insecticidal composition, to confer protection from insect damage are disclosed.

10 Claims, No Drawings
Specification includes a Sequence Listing.

CONTROL OF PLANT PESTS USING RNA MOLECULES

CROSS-REFERENCE TO RELATED APPLICATIONS

This application is a 371 National Stage application of International Application No. PCT/US2019/050716 filed Sep. 12, 2019, which claims priority to U.S. Provisional Application Ser. No. 62/730,712 filed on Sep. 13, 2018, the contents of these applications are incorporated by reference herein in their entirety.

SEQUENCE LISTING

A Sequence Listing in ASCII text format, submitted under 37 C.F.R. § 1.821, entitled "81661-WO-REG-ORG-P-1_5 T25.txt," 21,222,639 bytes in size, generated on Aug. 5, 2019 and filed via EFS-Web is provided in lieu of a paper copy. This Sequence Listing is hereby incorporated by reference into the specification for its disclosures in its entirety.

FIELD OF THE INVENTION

The invention relates generally to the control of pests that cause damage to crop plants by their feeding activities, and more particularly to the control of coleopteran and hemipteran pests by compositions comprising interfering RNA molecules. The invention further relates to the compositions and to methods of using such compositions comprising the interfering RNA molecules.

BACKGROUND

Commercial crops are often attacked by invertebrate pests such as insects. Compositions for controlling insect infestations in plants have typically been in the form of chemical insecticides. Good insect control can thus be reached, but these chemicals can sometimes also affect other, beneficial insects. Additional problems occur in areas of high insecticide use where populations of pest insects have become resistant to certain insecticides. This has been partially alleviated by various resistance management practices, but there is an increasing need for alternative pest control agents.

Insecticidal compositions that include the bacteria *Bacillus thuringiensis* ("Bt") have been commercially available and used as environmentally safe and acceptable bio-insecticides for more than thirty years. The effectiveness of these compositions is due to insecticidal proteins (called "Cry proteins") that are produced during the sporulation phase of the bacteria's growth cycle. Cry proteins are primarily active against the larval stages of pest insects and not active against the adult stage. Several native Cry proteins from Bt, for example, Cry1Ab, Cry1F, Cry2Aa and Cry34/Cry35, or engineered Cry proteins, for example modified Cry3A (mCry3A) or eCry3.1Ab, have also been expressed in transgenic crop plants, for example corn, and exploited commercially to control certain lepidopteran and coleopteran insect pests.

With the increased use of transgenic plants expressing Cry proteins, there have now been some reports that populations of pest insects in certain geographies have become tolerant or resistant to certain Cry proteins. Therefore, identifying alternative insect control agents with new modes of action, i.e. different from existing chemical insecticides and Cry proteins, would be beneficial. In addition, new biological insect control agents that may be toxic to multiple life stages of the target insect pest would be useful. Such insect control agents may include those that target genetic elements, such as genes that are essential to the growth and/or survival of a target insect pest.

RNA interference (RNAi) is a well-established technique to regulate gene expression, for example to down regulate gene expression, by using double-stranded RNA (dsRNA) or small interfering RNA (siRNA) to trigger degradation of mRNA of a gene of interest, thus preventing translation of a protein. RNAi has not only provided a means of functionally analyzing genes, but has been used for the effective control of pests, in particular plant insect pests. RNAi occurs when an organism recognizes double-stranded RNA (dsRNA) molecules and hydrolyzes them. The resulting hydrolysis products are siRNA fragments of about 19-24 nucleotides in length. The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant microRNAs (miRNAs) show extensive base pairing to, and guide cleavage of, their target mRNAs (Jones-Rhoades et al. (2006) *Annu. Rev. Plant Biol.* 57, 19-53; Llave et al. (2002) *Proc. Natl. Acad. Sci. USA* 97, 13401-13406). In other instances, interfering RNAs may bind to target RNA molecules having imperfect complementarity, causing translational repression without mRNA degradation. The majority of the animal miRNAs studied so far appear to function in this manner.

RNAi has been found to be useful for control of certain insect pests. RNAi strategies typically employ a synthesized, non-naturally occurring "interfering RNA", or "interfering RNA molecule" which typically comprises at least a RNA fragment against a target gene, a spacer sequence, and a second RNA fragment which is complementary to the first, so that a double-stranded RNA structure can be formed. This non-naturally occurring double-stranded RNA (dsRNA) takes advantage of the native RNAi pathways in the insect to trigger down-regulation of target genes that may lead to the cessation of feeding and/or growth and may result in the death of the insect pest.

Although it is known in the literature that RNAi strategies focused on certain target genes can lead to an insecticidal effect, for example in *Diabrotica* (corn rootworm) species, it is also known that not every target sequence is successful, and that an insecticidal effect cannot be predicted. For example, the overwhelming majority of sequences complementary to corn rootworm DNAs are not lethal in species of corn rootworm when used as dsRNA or siRNA. For example, Baum et al. ((2007) Nature Biotechnology 25:1322-1326), describe the effects of inhibiting several western corn rootworm (WCR) gene targets by RNAi. These authors reported that 8 of 26 target genes they tested were not able to provide experimentally significant WCR mortality, even at a very high iRNA (e.g., dsRNA) concentration of more than 520 ng/cm$^2$. Additionally, target genes against which a dsRNA molecule is known to give a strong RNAi effect in one insect species may not be a good target for different insect species. Whyard et al. ((2009) *Insect Biochemistry and Molecular Biology* 39: 824-832) report nearly 100-fold differences in efficacy when testing conspecific dsRNA molecules against a V-ATPase gene in four different insect species.

There is an ongoing need for compositions containing insecticidal active ingredients, and for methods of using such compositions, for instance for use in crop protection or insect-mediated disease control. Novel compositions are required to overcome the problem of resistance to existing insecticides and/or to help mitigate the development of resistance to existing transgenic plant approaches. Ideally such compositions have a high toxicity and are effective when ingested orally by the target pest and have applicability for use against the larval and/or adult stages of the pest insect. Thus any invention which provided compositions in which any of these properties was enhanced would represent a step forward in the art.

SUMMARY

The needs outlined above are met by the present invention which, in various embodiments, provides new compositions and methods of controlling economically important insect pests. More particularly, the invention provides compositions and methods of inhibiting expression of one or more target genes and proteins in coleopteran and/or hemipteran pests. More particularly, the invention encompasses compositions and methods of modulating expression of one or more target genes in coleopteran insect pests, such as *Sitophilus oryzae* (So; rice weevil), *Diabrotica virgifera virgifera* (Dv; western corn rootworm), *Diabrotica undecimpunctata howardi* (Du; southern corn rootworm), *Diabrotica barberi* (db; northern corn rootworm), *Phyllotreta armoraciae* (Pa; horseradish flea beetle), *Phyllotreta nemorum* (Pn; turnip flea beetle), *Phyllotreta cruciferae* (Pu; crucifer flea beetle), *Phyllotreta striolata* (Ps; striped flea beetle), *Phyllotreta atra* (Pt), *Psylliodes chrysocephala* (Pc; cabbage-stem flea beetle), *Meligethes aeneus* (Ma; pollen beetle), *Ceutorhynchus assimilis* (Ca; cabbage seedpod weevil), *Leptinotarsa decemlineata* (Ld; Colorado potato beetle), and/or in hemipteran insect pests, such as, *Nezara viridula* (Nv; green stink bug), *Euschistus heros* (Eh; brown stink bug), and *Piezodorus guildinii* (Pg; red-banded stink bug), and related species, that causes cessation of feeding, growth, development and reproduction, and eventually results in the death of the insect. A method of the invention comprises introduction of an interfering RNA molecule comprising a double-stranded RNA (dsRNA) or its modified forms such as small interfering RNA (siRNA) sequences, into cells or into the extracellular environment, such as the midgut, within a pest insect body wherein the dsRNA or siRNA enters the cells and inhibits expression of at least one or more target genes and wherein inhibition of the one or more target genes exerts a deleterious effect upon the pest insect. The interfering RNA molecule is non-naturally occurring. It is specifically contemplated that the methods and compositions of the invention will be useful in limiting or eliminating pest insect infestation in or on any plant by providing one or more compositions comprising interfering RNA molecules comprising dsRNA or siRNA molecules in the diet of the pest. The invention also provides interfering RNA molecules that, when delivered to a pest insect, inhibits through a toxic effect the ability of the pest insect to survive, grow, feed and/or reproduce, or to limit pest related feeding damage or loss to crop plants. Such delivery may be through production of the interfering RNA in a transgenic plant, for example corn, soybean, canola, rice, wheat and the like, or by topically applying a composition comprising the interfering RNA to a plant or plant seed, such as a corn plant or seed, or a soybean plant or seed, or a canola plant or seed, or a rice plant or seed, or a wheat plant or seed, and so forth. Delivery may further be through contacting the insect with the interfering RNA, such as when the insect feeds on plant material comprising the interfering RNA, either because the plant material is expressing the interfering RNA through a transgenic approach, or because the plant material is coated with a composition comprising the interfering RNA. The interfering RNA may also be provided in an artificial insect diet which the insect then contacts by feeding. The interfering RNA molecule comprises a nucleotide sequence that is complementary to a nucleotide sequence of a mRNA transcribable from a target gene or a portion of a nucleotide sequence of a mRNA transcribable from a target gene of the pest insect and therefore inhibits expression of the target gene, which causes cessation of feeding, growth, development, reproduction and eventually results in death of the pest insect. The invention is further drawn to nucleic acid constructs, nucleic acid molecules and recombinant vectors that comprise or encode at least a fragment of one strand of an interfering RNA molecule of the invention. The invention also provides chimeric nucleic acid molecules comprising an antisense strand of a dsRNA of the interfering RNA operably associated with a plant microRNA precursor molecule. The invention also provides artificial plant microRNA precursors comprising an antisense strand of a dsRNA of an interfering RNA of the invention.

In one aspect of the invention, an interfering ribonucleic acid (RNAi) molecule is provided wherein the RNAi molecule is encoded by a sequence comprising (a) any one of SEQ ID NOs:1-1814; (b) the complement of any one of SEQ ID NOs:1-1814; (c) at least 19 consecutive nucleotides of any one of SEQ ID NOs:1-1814; (d) the complement of at least 19 consecutive nucleotides of any one of SEQ ID NOs:1-1814; or (e) a sequence that hybridizes under stringent conditions with any of the aforementioned sequences, wherein said RNAi molecule post-transcriptionally silences an essential gene in a coleopteran and/or hemipteran pest insect.

In another aspect, the invention provides a double-stranded RNA (dsRNA) comprising annealed complementary strands, one strand of which comprises a sequence of at least 19 consecutive nucleotides which is wholly or partially complementary to a portion of a mRNA polynucleotide transcribable from a pest insect target gene, wherein the pest insect target gene comprises a coding sequence having from at least 90% to at least 99% identity to any one of SEQ ID NOs:1-1814, and wherein the strand of RNA having complementarity to said target gene is toxic to a coleopteran and/or hemipteran insect pest.

In another aspect of the invention, the RNAi or dsRNA is complementary to a portion of a target gene comprising any one of SEQ ID NOs:1815-3628.

In still another aspect of the invention, the RNAi or dsRNA comprises a nucleotide fragment that has at least 85% identity (e.g., at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, at least 100% identity) to any one of SEQ ID NOs:3629-5442. In one embodiment of this aspect the RNAi or dsRNA comprises any one of SEQ ID NOs:3629-5442.

In other aspect of the invention, the interfering RNA molecule has insecticidal activity on a coleopteran and/or a hemipteran plant pest. In some embodiments, the interfering molecule may comprise at least two dsRNAs, wherein each dsRNA comprises a sequence of nucleotides which is at least partially complementary to a target nucleotide sequence within the target gene. In further embodiments, each of the dsRNAs may comprise a different sequence of nucleotides which is complementary to a different target nucleotide sequence within the target gene.

The invention further provides compositions comprising one or more interfering RNA molecules comprising two or more of dsRNA molecules, wherein the two or more RNA molecules each comprise a different antisense strand, or comprising two or more nucleic acid constructs or nucleic acid molecules or artificial plant microRNA precursors of the invention.

The invention further provides insecticidal compositions for inhibiting the expression of a coleopteran and/or a hemipteran pest insect gene that comprises a dsRNA of the invention and an agriculturally acceptable carrier. In some embodiments, the coleopteran insect pest is selected from the group consisting of *Sitophilus oryzae* (So; rice weevil), *Diabrotica virgifera virgifera* (Dv; western corn rootworm), *Diabrotica undecimpunctata howardi* (Du; southern corn rootworm), *Diabrotica barberi* (db; northern corn rootworm), *Phyllotreta armoraciae* (Pa; horseradish flea beetle), *Phyllotreta nemorum* (Pn; turnip flea beetle), *Phyllotreta cruciferae* (Pu; crucifer flea beetle), *Phyllotreta striolata* (Ps; striped flea beetle), *Phyllotreta atra* (Pt), *Psylliodes chrysocephala* (Pc; cabbage-stem flea beetle), *Meligethes aeneus* (Ma; pollen beetle), *Ceutorhynchus assimilis* (Ca; cabbage seedpod weevil), *Leptinotarsa decemlineata* (Ld; Colorado potato beetle), and/or the hemipteran insect pest is selected from the group consisting of *Nezara viridula* (Nv; green stink bug), *Euschistus heros* (Eh; brown stink bug), and *Piezodorus guildinii* (Pg; red-banded stink bug). In some embodiments, inhibition of the expression of a target gene in a target insect pest of the invention leads to cessation of feeding and growth and ultimately results in the death of the target insect pest of the invention.

The invention is further drawn to transgenic plants which produce one or more interfering RNA molecules of the invention that are self-protected from insect feeding damage and to methods of using the plants alone or in combination with other insect control strategies to confer maximal insect control capabilities. Plants and/or plant parts producing one or more interfering RNA molecules of the invention or treated with a composition comprising one or more interfering RNA molecules of the invention are highly resistant to insect pest infestation. For example, economically important coleopteran pests can be controlled by a plant that produces an interfering RNA molecule of the invention or by a plant or plant seed that is treated with a composition comprising an interfering RNA molecule of the invention.

The invention also provides a method of controlling a coleopteran and/or hemipteran insect plant pest comprising contacting the coleopteran and/or hemipteran insect pest with a nucleic acid molecule that is or is capable of producing an interfering RNA of the invention for inhibiting expression of a gene in the coleopteran and/or hemipteran insect pest thereby controlling the coleopteran and/or hemipteran insect pest. In some aspects, the coleopteran insect pest is selected from the group consisting of the coleopteran insect pest is selected from the group consisting of *Sitophilus oryzae* (So; rice weevil), *Diabrotica virgifera virgifera* (Dv; western corn rootworm), *Diabrotica undecimpunctata howardi* (Du; southern corn rootworm), *Diabrotica barberi* (db; northern corn rootworm), *Phyllotreta armoraciae* (Pa; horseradish flea beetle), *Phyllotreta nemorum* (Pn; turnip flea beetle), *Phyllotreta cruciferae* (Pu; crucifer flea beetle), *Phyllotreta striolata* (Ps; striped flea beetle), *Phyllotreta atra* (Pt), *Psylliodes chrysocephala* (Pc; cabbage-stem flea beetle), *Meligethes aeneus* (Ma; pollen beetle), *Ceutorhynchus assimilis* (Ca; cabbage seedpod weevil), *Leptinotarsa decemlineata* (Ld; Colorado potato beetle), and/or the hemipteran insect pest is selected from the group consisting of *Nezara viridula* (Nv; green stink bug), *Euschistus heros* (Eh; brown stink bug), and *Piezodorus guildinii* (Pg; red-banded stink bug).

In other aspects, the invention provides a method of reducing an insect pest population on a transgenic plant expressing a second insecticidal agent, for example an insecticidal protein, in addition to an interfering RNA of the invention capable of inhibiting expression of an target gene in an insect pest, thereby reducing the pest insect population. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the second insecticidal agent may be derived from sources other than *B. thuringiensis*. The second insecticidal agent can be an agent selected from the group comprising a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphearicus* insecticidal protein, a *Chromobacterium* spp. insecticidal protein, a *Yersinia entomophaga* insecticidal protein, a *Paenibacillus popiliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia*, or *Yersinia*. In other embodiments, the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from *L sphaericus*. In still other embodiments, the insecticidal protein may be engineered or may be a hybrid or chimera of any of the preceding insecticidal proteins.

In other aspects, the invention provides a method of reducing resistance development in a pest insect population to an interfering RNA of the invention, the method comprising expressing in a transgenic plant fed upon by the pest insect population an interfering RNA of the invention that is capable of inhibiting expression of a target gene in a larval and adult insect pest, thereby reducing resistance development in the pest insect population compared to a pest insect population exposed to an interfering RNA capable of inhibiting expression of a pest insect gene described herein in only the larval stage or adult stage of an insect pest.

In other aspects, the invention provides a method of reducing the level of a target RNA transcribable from a pest insect target gene described herein in an insect comprising contacting the pest insect with a composition comprising an interfering RNA molecule of the invention, wherein the interfering RNA molecule reduces the level of the target RNA in a cell of the pest insect.

In still other aspects, the invention provides a method of conferring pest insect, particularly coleopteran and/or hemipteran pest insect, tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, thereby conferring to the plant or part thereof tolerance to the coleopteran and/or hemipteran pest insect.

In further aspects, the invention provides a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, thereby reducing root damage to the plant fed upon by a *Diabrotica* insect.

In other aspects, the invention provides a method of producing a transgenic plant cell having toxicity to a coleopteran and/or hemipteran pest insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the coleopteran and/or hemipteran insect compared to a control plant cell (e.g., a plant cell not comprising the interfering RNA molecule, the dsRNA, the nucleic acid molecule, the nucleic acid construct, the chimeric nucleic acid molecule, the artificial plant microRNA precursor molecule and/or the composition of the invention).

In further aspects, the invention provides a method of producing a transgenic plant having enhanced tolerance to coleopteran and/or hemipteran pest insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to coleopteran and/or hemipteran pest insect feeding damage compared to a control plant (e.g., a plant not comprising the interfering RNA molecule, the dsRNA, the nucleic acid molecule, the nucleic acid construct, the chimeric nucleic acid molecule, the artificial plant microRNA precursor molecule and/or the composition of the invention).

In other aspects, the invention provides a method of enhancing control of a coleopteran and/or hemipteran insect population comprising providing a transgenic plant or transgenic seed of the invention and applying to the transgenic plant or the transgenic seed a chemical pesticide that is insecticidal to a coleopteran and/or hemipteran insect, thereby enhancing control of the coleopteran and/or hemipteran insect population.

In other aspects, the invention provides a method of providing a corn grower with a means of controlling a coleopteran and/or hemipteran insect pest population below an economic threshold in a corn crop comprising (a) selling or providing to the grower transgenic corn seed comprising a dsRNA, a nucleic acid molecule, a nucleic acid construct, a chimeric nucleic acid molecule, an artificial plant microRNA precursor molecule and/or a composition of the invention; and (b) advertising to the grower that the transgenic corn seed produces transgenic corn plants capable of controlling a coleopteran and/or hemipteran insect pest population.

In another aspect, the invention provides a method of identifying an orthologous target gene for using as a RNAi strategy for the control of a plant pest, said method comprising the steps of: a) producing a primer pair that will amplify a target selected from the group comprising or consisting of SEQ ID NOs:7257-10884, or a complement thereof; b) amplifying an orthologous target gene from a nucleic acid sample of the plant pest; c) identifying a sequence of an orthologous target gene; d) producing an interfering RNA molecule, wherein the RNA comprises at least one dsRNA, wherein the dsRNA is a region of double-stranded RNA comprising annealed complementary strands, one strand of which comprises a sequence of at least 19 consecutive nucleotides which is at least partially complementary to the orthologous target nucleotide sequence within the target gene; and e) determining if the interfering RNA molecule of step (d) has insecticidal activity on the plant pest. If the interfering RNA has insecticidal activity on the plant pest target gene, an orthologous target gene for using in the control of a plant pest has been identified.

These and other aspects of the invention are set forth in more detail in the description of the invention below.

BRIEF DESCRIPTION OF THE SEQUENCES IN THE SEQUENCE LISTING

SEQ ID NOs:1-1814 are coding sequences of target genes from pest insects of the invention.

SEQ ID NOs:1815-3628 are fragments of DNA coding sequences from target genes (SEQ ID Nos:1-1814, respectively) used to synthesize interfering RNA molecules to test for insecticidal activity.

SEQ ID NOs:3629-5442 are RNA sequences of the fragments of the DNA coding sequences (SEQ ID NOs:1815-3628, respectively) used to synthesize interfering RNA molecules to test for insecticidal activity.

SEQ ID NO:5443-7256 are RNA sequences of the complete DNA coding sequences of the 112 target genes of SEQ ID NOs:1-1814, respectively.

SEQ ID NOs:7257-10884 are nucleotide sequences of forward and reverse primer pairs used to identify target genes (SEQ ID NOs:1-1814, respectively) from pest insects of the invention.

SEQ ID NOs:10885-12698 are amino acid sequences encoded by the target gene coding sequences (SEQ ID NOs:1-1814, respectively) from pest insects of the invention.

DETAILED DESCRIPTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art will recognize that modifications and variations in the embodiments described herein may be made without departing from the spirit or scope of the invention.

Definitions

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

For clarity, certain terms used in the specification are defined and presented as follows:

As used herein, "a," "an" or "the" can mean one or more than one. For example, "a cell" can mean a single cell or a multiplicity of cells.

As used herein, "and/or" refers to and encompasses any and all possible combinations of one or more of the associated listed items, as well as the lack of combinations when interpreted in the alternative, "or."

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, a "codon optimized" sequence means a nucleotide sequence wherein the codons are chosen to reflect the particular codon bias that a host cell or organism may have. This is typically done in such a way so as to preserve the amino acid sequence of the polypeptide encoded by the nucleotide sequence to be optimized. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

The terms "complementary" or "complementarity," refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands. Complementary polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

To "control" insects means to inhibit, through a toxic effect, the ability of insect pests to survive, grow, feed, or reproduce, or to limit insect-related damage or loss in crop plants or to protect the yield potential of a crop when grown in the presence of insect pests. To "control" insects may or may not mean killing the insects, although it preferably means killing the insects.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim and those that do not materially alter the basic and novel characteristic(s) of the claimed invention. Thus, the term "consisting essentially of" when used in a claim of this invention is not intended to be interpreted to be equivalent to "comprising."

To "deliver" a composition or toxic protein means that the composition or toxic protein comes in contact with an insect, which facilitates the oral ingestion of the composition or toxic protein, resulting in a toxic effect and control of the insect. The composition or toxic protein can be delivered in many recognized ways, including but not limited to, transgenic plant expression, formulated protein composition(s), sprayable protein composition(s), a bait matrix, or any other art-recognized protein delivery system.

"Effective insect-controlling amount" means that concentration of a toxic protein that inhibits, through a toxic effect, the ability of insects to survive, grow, feed or reproduce, or limits insect-related damage or loss in crop plants or protects the yield potential of a crop when grown in the presence of insect pests. "Effective insect-controlling amount" may or may not mean killing the insects, although it preferably means killing the insects.

"Expression cassette" as used herein means a nucleic acid molecule capable of directing expression of at least one polynucleotide of interest, such as a polynucleotide that encodes an interfering RNA molecule and/or a Cry protein of the invention, in an appropriate host cell, comprising a promoter operably linked to the polynucleotide of interest which is operably linked to a termination signal. An "expression cassette" also typically comprises additional polynucleotides required for proper translation of the polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is a defined region that is located within a genome and that, besides the aforementioned coding sequence, comprises other, primarily regulatory nucleic acid sequences responsible for the control of the expression, that is to say the transcription and translation, of the coding portion. A gene may also comprise other 5' and 3' untranslated sequences and termination sequences. Further elements that may be present are, for example, introns.

The term "heterologous" when used in reference to a gene or a polynucleotide or a polypeptide refers to a gene or a polynucleotide or a polypeptide that is or contains a part thereof not in its natural environment (i.e., has been altered by the hand of man) For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Insecticidal" is defined as a toxic biological activity capable of controlling insects, preferably by killing them.

The term "isolated" nucleic acid molecule, polynucleotide or protein is a nucleic acid molecule, polynucleotide or protein that no longer exists in its natural environment. An isolated nucleic acid molecule, polynucleotide or protein of the invention may exist in a purified form or may exist in a recombinant host such as in a transgenic bacteria or a transgenic plant. Therefore, a claim to an "isolated" nucleic acid molecule, as enumerated herein, encompasses a nucleic acid molecule when the nucleic acid molecule is comprised within a transgenic plant genome.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For an amino acid sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

The terms "sequence similarity" or "sequence identity" of nucleotide or amino acid sequences mean a degree of identity or similarity of two or more sequences and may be determined conventionally by using known software or computer programs such as the Best-Fit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482-489 (1981), to find the best segment of identity or similarity between two sequences. Sequence comparison between two or more polynucleotides or polypeptides is generally performed by comparing portions of the two sequences over a comparison window to identify and compare local regions of sequence similarity. The comparison window is generally from about 20 to 200 consecutive nucleotides. Gap performs global alignments: all of one sequence with all of another similar sequence using the method of Needleman and Wunsch, J. Mol. Biol. 48:443-453 (1970). When using a sequence alignment program such as BestFit to determine the degree of DNA sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a polynucleotide will hybridize to its target sequence to a detectably greater degree than other sequences (e.g., at least 2-fold over background). Stringent conditions are sequencedependent and will be different in different circumstances. By controlling the stringency of the hybridization and/or washing conditions, target polynucleotides can be identified which are 100% complementary to the probe (homologous probing). Alternatively, stringency conditions can be adjusted to allow some mismatching in sequences so that lower degrees of similarity are detected (heterologous probing). Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Moderate stringency conditions detect sequences that share at least 80% sequence identity. Exemplary moderate stringency conditions include hybridization in 40 to 45% formamide, 1 M NaCl, 1% SDS at 37° C., and a wash in 0.5× to 1×SSC at 55 to 60° C. High stringency conditions detect sequences that share at least 90% sequence identity. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267-284, 1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., eds., Greene Publishing and Wiley-Interscience, New York (1995). Methods of stringent hybridization are known in the art which conditions can be calculated by means known in the art. This is disclosed in Sambrook et al., Molecular Cloning: A Laboratory Manual, 2nd Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

A nucleic acid sequence is "isocoding with" a reference nucleic acid sequence when the nucleic acid sequence encodes a polypeptide having the same amino acid sequence as the polypeptide encoded by the reference nucleic acid sequence.

As used herein, "dsRNA" or "RNAi" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed. As used herein, the term "fully complementary" means that all the bases of the nucleotide sequence of the dsRNA are complementary to or 'match' the bases of the target nucleotide sequence. The term "at least partially complementary" means that there is less than a 100% match between the bases of the dsRNA and the bases of the target nucleotide sequence. The skilled person will understand that the dsRNA need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the dsRNA and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the dsRNA may comprise 1, 2 or 3 mismatches as compared with the target nucleotide sequence over every length of 24 partially complementary nucleotides. It will be appreciated by the person skilled in the art that the degree of complementarity shared between the dsRNA and the target nucleotide sequence may vary depending on the target gene to be down-regulated or depending on the insect pest species in which gene expression is to be controlled.

It will be appreciated that the dsRNA may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene. The skilled person will be aware of methods of identifying the most suitable target nucleotide sequences within the context of the full-length target gene. For example, multiple dsRNAs targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

Preferably, the % identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA, for example mRNA, and the GAP analysis aligns the two sequences over the full length of the target RNA.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. It is well-known in the art that small dsRNA of about 19-23 bp in length can be used to trigger gene silencing of a target gene. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 19 to about 23 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to a molecule that is double stranded for its full length, corresponding in size to a full length target RNA molecule. Bolognesi et al (2012, PLOS One, 7(10): e47534, herein incorporated by reference) teach that dsRNAs greater than or equal to about 60 bp are required for biological activity in artificial diet bioassays with Southern Corn Rootworm (SCR; *Diabrotica undecimpunctata howardii*).

Mao et al (2007, *Nature Biotechnology*, 35(11): 1307-1313) teach a transgenic plant expressing a dsRNA construct against a target gene (CYP6AE14) of an insect pest (cotton bollworm, *Helicoverpa armigera*). Insects feeding on the transgenic plant have small RNAs of about 19-23 bp in size of the target gene in their midgut, with a corresponding reduction in CYP6AE14 transcripts and protein. This suggests that the small RNAs were efficacious in reducing expression of the target gene in the insect pest. Therefore, small RNAs of about 19 bp, about 20 bp, about 21 bp, about 22 bp, about 23 bp, about 24 bp, about 25 bp, about 26 bp, about 27 bp, about 28 bp, about 29 bp, or about 30 bp may be efficacious in reducing expression of the target gene in an insect pest.

Alternatively, the dsRNA may comprise a target dsRNA of at least 19 base pairs, and the target dsRNA may be within a dsRNA "carrier" or "filler" sequence. For example, Bolognesi et al (2012) show that a 240 bp dsRNA encompassing a target dsRNA, which comprised a 21 bp consecutive sequence with 100% identity to the target sequence, had biological activity in bioassays with Southern Corn Rootworm. The present application exemplifies a similar approach in bioassays with Western Corn Rootworm. The target dsRNA may have a length of at least 19 to about 25 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs. Combined with the carrier dsRNA sequence, the dsRNA of the target sequence and the carrier dsRNA may have a total length of at least about 50 to about 100 base pairs, optionally a sequence of about 100 to about 200 base pairs, optionally a sequence of about 200 to about 500, and optionally a sequence of about 500 to about 1000 or more base pairs.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

The interfering RNAs of the current invention may comprise one dsRNA or multiple dsRNAs, wherein each dsRNA comprises or consists of a sequence of nucleotides which is at least partially complementary to a target nucleotide sequence within the target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single dsRNA i.e. repeats of a dsRNA that binds to a particular target nucleotide sequence within a specific target gene. In another embodiment, the dsRNAs within the interfering RNA comprise or consist of different sequences of nucleotides complementary to different target nucleotide sequences. It should be clear that combinations of multiple copies of the same dsRNA combined with dsRNAs binding to different target nucleotide sequences are within the scope of the current invention.

The dsRNAs may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the dsRNA(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions. Alternatively, the interfering RNA may be transcribed from a polynucleotide encoding the same. Thus, provided herein is an isolated polynucleotide encoding any of the interfering RNAs of the current invention.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, Cell, 116:281-297 (2004); Zhang et al. Dev. Biol. 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. Genes Dev. 16:1616-1626 (2002), Park et al. Curr. Biol. 12:1484-1495 (2002)) many hundreds have been identified. Furthermore, many plant miRNAs have been shown to be highly conserved across very divergent taxa. (Floyd et al. Nature 428:485-486 (2004); Zhang et al. Plant J. 46:243-259 (2006)). Many microRNA genes (MIR genes) have been identified and made publicly available in a database (miRBase, available via the World Wide Web). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. Proc. Natl. Acad. Sci. 105:9851-9852 (2008)). Many reviews on microRNA biogenesis and function are available, for example, see, Bartel Cell 116:281-297 (2004), Murchison et al. Curr. Opin. Cell Biol. 16:223-229 (2004), Dugas et al. Curr. Opin. Plant Biol. 7:512-520 (2004) and Kim Nature Rev. Mol. Cell Biol. 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA (mRNA). The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that of a non-native, heterologous miRNA (amiRNA/amiRNA*; e.g. siRNA/siRNA*) that is then processed into the mature miRNA sequence with the siRNA sequence.

In the context of the invention, the term "toxic" used to describe a dsRNA of the invention means that the dsRNA molecules of the invention and combinations of such dsRNA molecules function as orally active insect control agents that have a negative effect on an insect. When a composition of the invention is delivered to the insect, the result is typically death of the insect, or the insect does not feed upon the source that makes the composition available to the insect. Such a composition may be a transgenic plant expressing the dsRNA of the invention.

As used herein, a "coleopteran insect" refers to any member of the Order Coleoptera, including coleopteran plant pests. Non-limiting examples of coleopteran pest insects according to the invention include corn rootworm species in the Genus *Diabrotica*, such as *Diabrotica barberi* (northern corn rootworm; NCR), *D. virgifera virgifera* (western corn rootworm; WCR), *D. undecimpunctata howardii* (southern corn rootworm; SCR), *D. virgifera zeae* (Mexican corn rootworm; MCR) and *D. speciose; Leptinotarsa* spp. such as *L. decemlineata* (Colorado potato beetle); *Chrysomela* spp. such as *C. scripta* (cottonwood leaf beetle; CLB); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil; PW); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (white grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (bean leaf beetle); *Epicauta* spp. such as *E. pestifera* and *E. lemniscata* (blister beetles); and any combination of the foregoing.

As used herein, a "hemipteran insect" refers to any member of the Order Hemiptera, including hemipteran plant pests. Non-limiting examples of hemipteran pest insects according to the invention include *Euschistus heros* (brown stinkbug), *Nezara viridula* (green stinkbug) and *Piezodorus guildinii* (red banded stinkbug).

The term "agrochemically active ingredient" refers to chemicals and/or biological compositions, such as those described herein, which are effective in killing, preventing, or controlling the growth of undesirable pests, such as, plants, insects, mice, microorganism, algae, fungi, bacteria, and the like (such as pesticidally active ingredients). An interfering RNA molecule of the invention is an agrochemically active ingredient.

An "agriculturally acceptable carrier" includes adjuvants, mixers, enhancers, etc. beneficial for application of an active ingredient, such as an interfering RNA molecule of the invention. Suitable carriers should not be phytotoxic to valuable crops, particularly at the concentrations employed in applying the compositions in the presence of crops, and should not react chemically with the compounds of the active ingredient herein, namely an interfering RNA of the invention, or other composition ingredients. Such mixtures can be designed for application directly to crops, or can be concentrates or formulations which are normally diluted with additional carriers and adjuvants before application. They may include inert or active components and can be solids, such as, for example, dusts, granules, water dispersible granules, or wettable powders, or liquids, such as, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like.

For the present invention, an agriculturally acceptable carrier may also include non-pathogenic, attenuated strains of microorganisms, which carry the insect control agent, namely an interfering RNA molecule of the invention. In this case, the microorganisms carrying the interfering RNA may also be referred to as insect control agents. The microorganisms may be engineered to express a nucleotide sequence of a target gene to produce interfering RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the interfering RNA molecules or fragments or derivatives thereof.

In another embodiment, the interfering RNA molecules may be encapsulated in a synthetic matrix such as a polymer and applied to the surface of a host such as a plant. Ingestion of the host cells by an insect permits delivery of the insect control agents to the insect and results in down-regulation of a target gene in the host.

A composition of the invention, for example a composition comprising an interfering RNA molecule of the invention and an agriculturally acceptable carrier, may be used in conventional agricultural methods. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

In the context of the invention, a number in front of the suffix "mer" indicates a specified number of subunits. When applied to RNA or DNA, this specifies the number of bases in the molecule. For example, a 19 nucleotide subsequence of an mRNA having the sequence ACUGGUCGCGUUG-CAUGCU is a "19-mer."

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A corn rootworm "transcriptome" is a collection of all or nearly all the ribonucleic acid (RNA) transcripts in a corn rootworm cell.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated herein by their bases by the following standard abbreviations: adenine (A), cytosine (C), thymine (T), and guanine (G) Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The invention is based on the unexpected result that double stranded RNA (dsRNA) or small interfering RNAs (siRNA) designed to target a mRNA transcribable from a pest insect essential gene described herein are toxic to the pest insect and can be used to control pest insect infestation of a plant and impart to a transgenic plant tolerance to a pest insect infestation, particularly a coleopteran and/or hemipteran pest insect infestation. Thus, in one embodiment, the invention provides a double stranded RNA (dsRNA) molecule comprising a sense strand and an antisense strand, wherein a nucleotide sequence of the antisense strand is complementary to a portion of a mRNA polynucleotide transcribable from a pest insect gene described herein, wherein the dsRNA molecule is toxic to a pest insect, particularly to a coleopteran and/or a hemipteran pest insect.

The present invention relates to an RNA encoded by the sequence comprising any one of SEQ ID NOs:1-1814, any at least 19 nucleotide fragment of any one of SEQ ID NOs:1-1814, the complement of any at least 19 nucleotide fragment of any one of SEQ ID NOs:1-1814, or a sequence that hybridizes under stringent conditions with any of the aforementioned sequences, wherein said RNA post transcriptionally silences an essential gene in a plant pest organism.

It is known in the art that dsRNA molecules that are not perfectly complementary to a target sequence (for example, having only 95% identity to the target gene) are effective to control coleopteran pests (see, for example, Narva et al., U.S. Pat. No. 9,012,722). The invention provides an interfering RNA molecule comprising at least one dsRNA, where the dsRNA is a region of double-stranded RNA comprising annealed at least partially complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides which is at least partially complementary to a target nucleotide sequence within an insect pest target gene. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of SEQ ID NO:3629-7256, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of SEQ ID NO:3629-7256, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of a nucleotide sequence encoding an amino acid sequence encoded by SEQ ID NO:3629-7256, or the complement thereof, or (iv) can hybridize under stringent conditions to a polynucleotide selected from the group consisting of SEQ ID NO:3629-7256, and the complements thereof, wherein the interfering RNA molecule has insecticidal activity on a coleopteran and/or hemipteran plant pest. In some embodiments, the interfering RNA molecule comprises a nucleotide fragment that has at least 85% identity (e.g., at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity) to any one of SEQ ID Nos:3629-7256, or a complement thereof.

In some embodiments, the interfering RNA molecule comprises at least two dsRNAs, wherein each dsRNA comprises a sequence of nucleotides which is at least partially complementary to a target nucleotide sequence within the target gene. In some embodiments the target gene comprises any one of SEQ ID NOs:1-1814. In some embodiments, each of the dsRNAs comprise a different sequence of nucleotides which is complementary to a different target nucleotide sequence within the target gene. In other embodiments, each of the dsRNAs comprise a different sequence of nucleotides which is complementary to a target nucleotide sequence within two different target genes.

In some embodiments, the interfering RNA molecule comprises a dsRNA that can comprise, consist essentially of or consist of from at least 18 to about 25 consecutive nucleotides (e.g. 18, 19, 20, 21, 22, 23, 24, 25, 26, 27, 28, or 29) to at least about 300 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the interfering RNA molecule comprises a dsRNA which comprises an antisense strand that is complementary to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NO:3629-7256, or the complement thereof. In other embodiments, the portion of dsRNA comprises, consists essentially of or consists of at least from 19, 20 or 21 consecutive nucleotides to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NO:3629-7256, or the complement thereof. In some embodiments, the portion of the dsRNA comprises a nucleotide fragment that has at least 85% identity (e.g., at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity) to any one of SEQ ID Nos:3629-7256, or a complement thereof.

In other embodiments, an interfering RNA molecule of the invention comprises a dsRNA which comprises, consists essentially of or consists of any 21-mer subsequence of any one of SEQ ID NOs:5443-7256 consisting of N to N+20 nucleotides, or any complement thereof. For example, an interfering RNA molecule of the invention comprises a dsRNA which comprises, consist essentially of or consists of any 21-mer subsequence of SEQ ID NO:5443, wherein N is nucleotide 1 to nucleotide 201 of SEQ ID NO:5443, or any complement thereof. In other words, the portion of the mRNA that is targeted comprises any of the 2020 21 consecutive nucleotide subsequences i.e. 21-mers, of SEQ ID NO:5443, or any of their complementing sequences.

In still other embodiments, the interfering RNA molecule of the invention comprises a dsRNA which comprises, consists essentially of or consists of SEQ ID NO:3629-7256, or the complement thereof.

In other embodiments, the interfering RNA molecule comprises the antisense strand of a dsRNA of the invention which comprises, consists essentially of or consists of the antisense of any one of nucleotide sequences SEQ ID NOs:3629-7256. The nucleotide sequence of the antisense strand of a dsRNA of the invention can have one nucleotide at either the 3' or 5' end deleted or can have up to six nucleotides added at the 3' end, the 5' end or both, in any combination to achieve an antisense strand consisting essentially of any 19-mer, any 20-mer, or any 21-mer nucleotide sequence, as it would be understood that the deletion of the one nucleotide or the addition of up to the six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3' end may be present, which is used to stabilize the siRNA duplex and does not affect the specificity of the siRNA.

In some embodiments of the invention, the antisense strand of the double stranded RNA of the interfering RNA molecule can be fully complementary to the target RNA polynucleotide or the antisense strand can be substantially complementary or partially complementary to the target RNA polynucleotide. The dsRNA of the interfering RNA molecule may comprise a dsRNA which is a region of double-stranded RNA comprising substantially complementary annealed strands, or which is a region of double-stranded RNA comprising fully complementary annealed strands. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siR-NAs enhance selective gene silencing of a mutant ALS-causing Allele1" *Acta Pharmacol. Sin.* 29:211-216 (2008); Schwarz et al. "Asymmetry in the assembly of the RNAi enzyme complex" *Cell* 115:199-208 (2003)).

In some embodiments of the invention, the interfering RNA comprises a dsRNA which comprises a short hairpin RNA (shRNA) molecule. Expression of shRNA in cells is typically accomplished by delivery of plasmids or recombinant vectors, for example in transgenic plants such as transgenic corn.

The invention encompasses a nucleic acid construct comprising an interfering RNA of the invention. The invention further encompasses a nucleic acid molecule encoding at least one interfering molecule of the invention. The invention further encompasses a nucleic acid construct comprising at least one interfering molecule of the invention or comprising a nucleic acid molecule encoding the at least one interfering molecule of the invention. The invention further encompasses a nucleic acid construct wherein the nucleic acid construct is an expression vector. The invention further encompasses a recombinant vector comprising a regulatory sequence operably linked to a nucleotide sequence that encodes an interfering RNA molecule of the invention. A regulatory sequence may refer to a promoter, enhancer, transcription factor binding site, insulator, silencer, or any other DNA element involved in the expression of a gene.

The invention further encompasses chimeric nucleic acid molecules comprising an interfering RNA molecule with an antisense strand of a dsRNA operably linked with a plant microRNA precursor molecule. In some embodiments, the chimeric nucleic acid molecule comprises an antisense strand having the nucleotide sequence of any of the 21-mer subsequences of any one of SEQ ID NOs:5443-7256, or any complement thereof, operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA of an interfering RNA molecule of the invention. In other embodiments, the artificial plant microRNA precursor molecule comprises an antisense strand having the nucleotide sequence of any of the 19-mer, 20-mer, or 21-mer subsequences of the antisense of any one of SEQ ID NOs:5443-7256. The use of artificial plant microRNAs to deliver a nucleotide sequence of interest (e.g., an artificial miRNA; siRNA/siRNA*) into a plant is known in the art (see, e.g., Schwab et al. 2006. The Plant Cell 18:1121-1133). In the invention, the artificial microR-NAs are chimeric or hybrid molecules, having a plant microRNA precursor backbone and an insect siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Non-limiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses interfering RNA molecules, nucleic acid constructs, nucleic acid molecules or recombinant vectors comprising at least one strand of a dsRNA of an interfering RNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

Plant pest insects that are targets of the present invention include those insects in the Orders Coleoptera (beetles), Lepidoptera (moths, butterflies), Diptera (flies), Protura, Collembola (springtails), Diplura, Microcoryphia (jumping bristletails), Thysanura (bristletails, silverfish), Ephemeroptera (mayflies), Odonata (dragonflies, damselflies), Orthoptera (grasshoppers, crickets, katydids), Phasmatodea (walkingsticks), Grylloblattodea (rock crawlers), Mantophasmatodea, Dermaptera (earwigs), Plecoptera (stoneflies), Embioptera (web spinners), Zoraptera, Isoptera (termites), Mantodea (mantids), Blattodea (cockroaches), Hemiptera (true bugs, cicadas, leafhoppers, aphids, scales), Thysanoptera (thrips), Psocoptera (book and bark lice), Phthiraptera (lice; including but not limited to suborders Amblycera, Ischnocera and Anoplura), Neuroptera (lacewings, owlflies, mantispids, antlions), Hymenoptera (bees, ants, wasps), Trichoptera (caddisflies), Siphonaptera (fleas), Mecoptera (scorpion flies), Strepsiptera (twisted-winged parasites), and preferably in the Orders Coleoptera and/or Hemiptera.

More preferably, target insect pests of the invention are selected from the group consisting of the coleopteran insect pests *Sitophilus oryzae* (So; rice weevil), *Diabrotica virgifera virgifera* (Dv; western corn rootworm), *Diabrotica undecimpunctata howardi* (Du; southern corn rootworm), *Diabrotica barberi* (db; northern corn rootworm), *Phyllotreta armoraciae* (Pa; horseradish flea beetle), *Phyllotreta nemorum* (Pn; turnip flea beetle), *Phyllotreta cruciferae* (Pu; crucifer flea beetle), *Phyllotreta striolata* (Ps; striped flea beetle), *Phyllotreta atra* (Pt; flea beetle), *Psylliodes chrysocephala* (Pc; cabbage-stem flea beetle), *Meligethes aeneus* (Ma; pollen beetle), *Ceutorhynchus assimilis* (Ca; cabbage seedpod weevil), *Leptinotarsa decemlineata* (Ld; Colorado potato beetle), and/or the hemipteran insect pest is selected from the group consisting of *Nezara viridula* (Nv; green stink bug), *Euschistus heros* (Eh; brown stink bug), and *Piezodorus guildinii* (Pg; red-banded stink bug).

In some embodiments, the insect pest is a *Sitophilus* species, preferably *Sitophilus oryzae*, and a gene that is targeted by a dsRNA of the invention comprises, consists essentially of or consists of any one of SEQ ID NOs:1-116, the complement of any one of SEQ ID NOs:1-116, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1-116, the complement of any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1-116 or a sequence that can hybridize under stringent conditions with any of the aforementioned sequences; wherein said RNA is effective in inhibiting expression of a target sequence in a *Sitophilus* species. Preferably, the sequence is or comprises any one of SEQ ID NOs:3629-3744, the complement of any one of SEQ ID NOs:3629-3744, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NOs:3629-3744 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:3629-3744.

In some embodiments, the insect pest is a *Diabrotica* species, preferably a *Diabrotica* species selected from the group consisting of *D. virgifera virgifera* (Dv; western corn rootworm), *D. undecimpunctata howardi* (Du; southern corn rootworm) and *Diabrotica barberi* (db; northern corn rootworm). In some embodiments, the pest is *Diabrotica virgifera* (Dv) and a gene that is targeted by a dsRNA of the invention comprises, consists essentially of or consists of any one of SEQ ID NOs:117-228, the complement of any one of SEQ ID NOs:117-228, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:117-228, the complement of any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:117-228 or a sequence that can hybridize under stringent conditions with any of the aforementioned sequences; wherein said RNA is effective in inhibiting expression of a target sequence in a Dv pest. Preferably, the sequence is or comprises any one of SEQ ID NOs:3745-3856, the complement of any one of SEQ ID NOs:3745-3856, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:3745-3856 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:3745-3856.

In some embodiments, the pest is *Diabrotica undecimpunctata* (Du) and a gene that is targeted by a dsRNA of the invention comprises, consists essentially of or consists of any one of SEQ ID NOs:229-340, the complement of any one of SEQ ID NOs:229-340, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:229-340, the complement of any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:229-340 or a sequence that can hybridize under stringent conditions with any of the aforementioned sequences; wherein said RNA is effective in inhibiting expression of a target sequence in a Du pest. Preferably, the sequence is or comprises any one of SEQ ID NOs:3857-3968, the complement of any one of SEQ ID NOs:3857-3968, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:3857-3968 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:3857-3968.

In some embodiments, the pest is *Diabrotica barberi* (db) and a gene that is targeted by a dsRNA of the invention comprises, consists essentially of or consists of any one of SEQ ID NOs:341-451, the complement of any one of SEQ ID NOs:341-451, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:341-451, the complement of any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:341-451 or a sequence that can hybridize under stringent conditions with any of the aforementioned sequences; wherein said RNA is effective in inhibiting expression of a target sequence in a db pest. Preferably, the sequence is or comprises any one of SEQ ID NOs:3969-4079, the complement of any one of SEQ ID NOs:3969-4079, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:3969-4079 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:3969-4079.

In some embodiments, the insect pest is a flea beetle pest species, preferably the flea beetle pest species selected from the group consisting of *Phyllotreta armoraciae* (Pa; horseradish flea beetle), *Phyllotreta nemorum* (Pn; turnip flea beetle), *Phyllotreta cruciferae* (Pu; crucifer flea beetle), *Phyllotreta striolata* (Ps; striped flea beetle), *Phyllotreta atra* (Pt; flea beetle) and *Psylliodes chrysocephala* (Pc; cabbage-stem flea beetle). In some embodiments the pest is *Phyllotreta armoraciae* (Pa) and a gene that is targeted by a dsRNA of the invention comprises, consists essentially of or consists of any one of SEQ ID NOs:452-564, the complement of any one of SEQ ID NOs:452-564, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:452-564, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:452-564 or a sequence that hybridizes under stringent conditions with any of the aforementioned sequences; wherein said RNA is effective in inhibiting expression of a target sequence in the Pa pest. Preferably, the sequence is or comprises any one of SEQ ID NOs:4080-4192, the complement of SEQ ID NOs: 4080-4192, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4080-4192 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4080-4192.

In some embodiments the pest is *Phyllotreta nemorum* (Pn) and a gene that is targeted by a dsRNA of the invention comprises, consists essentially of or consists of any one of SEQ ID NOs:565-679, the complement of any one of SEQ ID NOs:565-679, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:565-679, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:565-679 or a sequence that hybridizes under stringent conditions with any of the aforementioned sequences; wherein said RNA is effective in inhibiting expression of a target sequence in the Pn pest. Preferably, the sequence is or comprises any one of SEQ ID NOs:4193-4307, the complement of SEQ ID NOs:4193-4307, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4193-4307 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4193-4307.

In some embodiments the pest is *Phyllotreta cruciferae* (Pu) and a gene that is targeted by a dsRNA of the invention comprises, consists essentially of or consists of any one of SEQ ID NOs:680-789, the complement of any one of SEQ ID NOs:680-789, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:680-789, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:680-789 or a sequence that hybridizes under stringent conditions with any of the aforementioned sequences; wherein said RNA is effective in inhibiting expression of a target sequence in the Pu pest. Preferably, the sequence is or comprises any one of SEQ ID NOs:4308-4417, the complement of SEQ ID NOs:4308-4417, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4308-4417 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4308-4417.

In some embodiments the pest is *Phyllotreta striolata* (Ps) and a gene that is targeted by a dsRNA of the invention comprises, consists essentially of or consists of any one of SEQ ID NOs:790-905, the complement of any one of SEQ ID NOs:790-905, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:790-905, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:790-905 or a sequence that hybridizes under stringent conditions with any of the aforementioned sequences; wherein said RNA is effective in inhibiting expression of a target sequence in the Ps pest. Preferably, the sequence is or comprises any one of SEQ ID NOs:4418-4533, the complement of SEQ ID Nos:4418-4533, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4418-4533 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4418-4533.

In some embodiments the pest is *Phyllotreta atra* (Pt) and a gene that is targeted by a dsRNA of the invention comprises, consists essentially of or consists of any one of SEQ ID NOs:906-1020, the complement of any one of SEQ ID NOs:906-1020, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:906-1020, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:906-1020 or a sequence that hybridizes under stringent conditions with any of the aforementioned sequences; wherein said RNA is effective in inhibiting expression of a target sequence in the Pt pest. Preferably, the sequence is or comprises any one of SEQ ID NOs:4534-4648, the complement of SEQ ID NOs:4534-4648, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4534-4648 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4534-4648.

In some embodiments the pest is *Psylliodes chrysocephala* (Pc) and a gene that is targeted by a dsRNA of the invention comprises, consists essentially of or consists of any one of SEQ ID NOs:1021-1133, the complement of any one of SEQ ID NOs:1021-1133, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1021-1133, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1021-1133 or a sequence that hybridizes under stringent conditions with any of the aforementioned sequences; wherein said RNA is effective in inhibiting expression of a target sequence in the Pc pest. Preferably, the sequence is or comprises any one of SEQ ID NOs:4649-4761, the complement of SEQ ID NOs:4649-4761, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4649-4761 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4649-4761.

In some embodiments the pest is *Meligethes aeneus* (Ma) and a gene that is targeted by a dsRNA of the invention comprises, consists essentially of or consists of any one of SEQ ID NOs:1134-1248, the complement of any one of SEQ ID NOs:1134-1248, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1134-1248, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1134-1248 or a sequence that hybridizes under stringent conditions with any of the aforementioned sequences; wherein said RNA is effective in inhibiting expression of a target sequence in the Ma pest. Preferably, the sequence is or comprises any one of SEQ ID NOs:4762-4876, the complement of any one of SEQ ID NOs:4762-4876, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4762-4876 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4762-4876.

In some embodiments the pest is *Ceutorhynchus assimilis* (Ca) and a gene that is targeted by a dsRNA of the invention comprises, consists essentially of or consists of any one of SEQ ID NOs:1249-1360, the complement of any one of SEQ ID NOs:1249-1360, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1249-1360, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1249-1360 or a sequence that hybridizes under stringent conditions with any of the aforementioned sequences; wherein said RNA is effective in inhibiting expression of a target sequence in the Ca pest. Preferably, the sequence is or comprises any one of SEQ ID NOs:4877-4988, the complement of any one of SEQ ID NOs:4877-4988, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4877-4988 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4877-4988.

In some embodiments, the insect pest is a hemipteran insect pest, preferably a hemipteran insect pest selected from the group consisting of *Nezara viridula* (Nv), *Euschistus heros* (Eh) and *Piezodorus guildinii* (Pg). In some embodiments the insect pest is *Nezara viridula* (Nv), and a gene that is targeted by a dsRNA of the invention comprises, consists essentially of or consists of any one of SEQ ID NOs:1361-1473, the complement of any one of SEQ ID NOs:1361-1473, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1361-1473, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1361-1473 or a sequence that hybridizes under stringent conditions with any of the aforementioned sequences; wherein said RNA is effective in inhibiting expression of a target sequence in the Nv pest. Preferably, the sequence is or comprises any one of SEQ ID NOs:4989-5101, the complement of any one of SEQ ID NOs:4989-5101, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:4989-5101 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:4989-5101.

In some embodiments, the insect pest is *Euschistus heros* (Eh) and a gene that is targeted by a dsRNA of the invention comprises, consists essentially of or consists of any one of SEQ ID NOs:1474-1586, the complement of any one of SEQ ID NOs:1474-1586, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1474-1586, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1474-1586 or a sequence that hybridizes under stringent conditions with any of the aforementioned sequences; wherein said RNA is effective in inhibiting expression of a target sequence in the Eh pest. Preferably, the sequence is or comprises any one of SEQ ID NOs:5102-5214, the complement of any one of SEQ ID NOs:5102-5214, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:5102-5214 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:5102-5214.

In some embodiments, the insect pest is *Piezodorus guildinii* (Pg) and a gene that is targeted by a dsRNA of the invention comprises, consists essentially of or consists of any one of SEQ ID NOs:1587-1699, the complement of any one of SEQ ID NOs:1587-1699, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1587-1699, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1587-1699 or a sequence that hybridizes under stringent conditions with any of the aforementioned sequences; wherein said RNA is effective in inhibiting expression of a target sequence in the Pg pest. Preferably, the sequence is or comprises any one of SEQ ID NOs:5215-5327, the complement of any one of SEQ ID NOs:5215-5327, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:5215-5327 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:5215-5327.

In some embodiments, the insect pest is *Leptinotarsa decimlineata* (Ld) and a gene that is targeted by a dsRNA of the invention comprises, consists essentially of or consists of any one of SEQ ID NOs:1700-1814, the complement of any one of SEQ ID NOs:1700-1814, any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1700-1814, the complement of any at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 or more nucleotide fragment of any one of SEQ ID NOs:1700-1814 or a sequence that hybridizes under stringent conditions with any of the aforementioned sequences; wherein said RNA is effective in inhibiting expression of a target sequence in the Ld pest. Preferably, the sequence is or comprises any one of SEQ ID NOs:5328-5442, the complement of any one of SEQ ID NOs:5328-5442, any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with any one of SEQ ID NOs:5328-5442 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of any one of SEQ ID NOs:5328-5442.

In some embodiments, the invention encompasses a composition comprising one or more or two or more of the interfering RNA molecules of the invention. In some embodiments, the interfering RNA molecules are present on the same nucleic acid construct, on different nucleic acid constructs, or any combination thereof. For example, one interfering RNA molecule of the invention may be present on a nucleic acid construct, and a second interfering RNA molecule of the invention may be present on the same nucleic acid construct or on a separate, second nucleic acid construct. The second interfering RNA molecule of the invention may be to the same target gene or to a different target gene.

In some embodiments, the invention encompasses a composition comprising an interfering RNA molecule which comprises at least one dsRNA wherein the dsRNA is a region of double-stranded RNA comprising annealed complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides which is at least partially complementary to a target nucleotide sequence within a target gene comprising, consisting essentially of or consisting of any one of SEQ ID NOs:1-1814. In some embodiments, the interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:3629-7256, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:3629-7256 or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of a nucleotide sequence encoding an amino acid sequence encoded by any one of SEQ ID NOs:3629-7256, or the complement thereof, or (iv) can hybridize under stringent conditions to a polynucleotide selected from the group consisting of any one of SEQ ID NOs:3629-7256, and the complements thereof.

In some embodiments, the invention encompasses compositions comprising an interfering RNA molecule comprising two or more dsRNAs, wherein the two or more dsRNAs each comprise a different antisense strand. In some embodiments the invention encompasses compositions comprising at least two or more interfering RNA molecules, wherein the two or more interfering RNA molecules each comprise a dsRNA comprising a different antisense strand. The two or more interfering RNAs may be present on the same nucleic acid construct, on different nucleic acid constructs or any combination thereof. In other embodiments, the composition comprises a RNA molecule comprising an antisense strand consisting essentially of a nucleotide sequence comprising at least a 19 consecutive nucleotide fragment of any one of SEQ ID NOs:5443-7256, and in some embodiments may further comprise an RNA molecule comprising an antisense strand consisting essentially of a second nucleotide sequence comprising at least a 19 consecutive nucleotide fragment of any one of SEQ ID NOs:5443-7256; and in some embodiments may further comprise an RNA molecule comprising an antisense strand consisting essentially of a third nucleotide sequence comprising at least a 19 consecutive nucleotide fragment of the antisense any one of SEQ ID NOs: 5443-7256, and in some embodiments may further comprise an RNA molecule comprising an antisense strand consisting essentially of a fourth nucleotide sequence comprising at least a 19 consecutive nucleotide fragment of the antisense any one of SEQ ID NOs:5443-7256, and in some embodiments may further comprise an RNA molecule comprising an antisense strand consisting essentially of a fifth nucleotide sequence comprising at least a 19 consecutive nucleotide fragment of the antisense of SEQ ID NOs:5443-7256, and in some embodiments may further comprise an RNA molecule comprising an antisense strand consisting essentially of a sixth nucleotide sequence comprising at least a 19 consecutive nucleotide fragment of the antisense of any one of SEQ ID NOs:5443-7256, and in some embodiments may further comprise an RNA molecule comprising an antisense strand consisting essentially of a seventh nucleotide sequence comprising at least a 19 consecutive nucleotide fragment of the antisense of any one of SEQ ID NOs:5443-7256. In other embodiments, the composition may comprise two or more of the nucleic acid molecules, wherein the two or more nucleic acid molecules each encode a different interfering RNA molecule. In other embodiments, the composition may comprise two or more of the nucleic acid constructs, wherein the two or more nucleic acid constructs each comprise a nucleic acid molecule encoding a different interfering RNA.

In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

In some embodiments, the invention encompasses an insecticidal composition for inhibiting the expression of an insect pest gene described herein, comprising at least one interfering RNA of the invention and/or the DNA encoding it and/or the expression construct of the invention and/or a cell (active or inactivated) expressing the RNA molecule of the invention and an agriculturally acceptable carrier. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

In some embodiments, an acceptable agricultural carrier is a formulation useful for topically applying the insecticidal composition comprising the interfering RNA molecule to a plant or seed. In some embodiments, the formulation may be in any form suitable for application to a plant, a seed or directly to a target insect pest. In one aspect, the formulation may be in solid form (powder, pellet, or a bait), liquid form, or gel form. In some embodiments, the interfering RNA molecules are stabilized against degradation because of their double stranded nature and the introduction of Dnase/Rnase inhibitors. For example, dsRNA or siRNA can be stabilized by including thymidine or uridine nucleotide 3' overhangs. The dsRNA or siRNA contained in the compositions of the invention can be chemically synthesized at industrial scale in large amounts. Methods available would be through chemical synthesis or through the use of a biological agent.

In other embodiments the formulation comprises a transfection promoting agent. In other embodiments, the transfection promoting agent is a lipid-containing compound. In further embodiments, the lipid-containing compound is selected from the group consisting of; Lipofectamine, Cellfectin, DMRIE-C, DOTAP and Lipofectin. In another embodiment, the lipid-containing compound is a Tris cationic lipid.

In some embodiments, the formulation further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. In some embodiments, the nucleic acid condensing agent is spermidine or protamine sulfate.

In still further embodiments, the formulation further comprises buffered sucrose or phosphate buffered saline.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

In order to apply an active ingredient to insects and/or crops of useful plants as required by the methods of the invention said active ingredient may be used in pure form or, more typically, formulated into a composition which includes, in addition to said active ingredient, a suitable inert diluent or carrier and optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). SFAs include non-ionic, cationic and/or anionic surfactants, as well as surfactant mixtures. Thus in further embodiments according to any aspect of the invention mentioned hereinbefore, the active ingredient will be in the form of a composition additionally comprising an agriculturally acceptable carrier or diluent.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the active ingredient.

Dustable powders (DP) may be prepared by mixing the active ingredient with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing the active ingredient with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing the active ingredient with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of the active ingredient and one or more powdered solid diluents or carriers, or from pre-formed blank granules by absorbing the active ingredient (or a solution thereof, in a suitable agent) in a porous granular material (such as pumice, attapulgite clays, fuller's earth, kieselguhr, diatomaceous earths or ground corn cobs) or by adsorbing the active ingredient (or a solution thereof, in a suitable agent) on to a hardcore material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible concentrates (DC) may be prepared by dissolving the active ingredient in water or an organic solvent, such as a ketone, alcohol or glycol ether. These solutions may contain a surface active agent (for example to improve water dilution or prevent crystallisation in a spray tank). Emulsifiable concentrates (EC) or oil-in-water emulsions (EW) may be prepared by dissolving the active ingredient in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 15060 and SOLVESSO 200; SOLVESSO is a Registered TradeMark), ketones (such as cyclohexanone or methylcyclohexanone) and alcohols (such as benzyl alcohol, furfuryl alcohol or butanol), N-alkylpyrrolidones (such as N-methylpyrrolidoneor N-octylpyrrolidone), dimethyl amides of fatty acids (such as C8-C10 fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining the active ingredient either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. The active ingredient is present initially in either the water or the solvent/SPA blend. Suitable solvents for use in MEs include those hereinbefore described for use in ECs or in EWs. A ME may be either an oil-in-water or a water-in-oil system (which system is present may be determined by conductivity measurements) and may be suitable for mixing water-soluble and oil-soluble pesticides in the same formulation. A ME is suitable for dilution into water, either remaining as a microemulsion or forming a conventional oil-in-water emulsion.

Suspension concentrates (SC) may comprise aqueous or non-aqueous suspensions of finely divided insoluble solid particles of the active ingredient. SCs may be prepared by ball or bead milling the solid active ingredient in a suitable medium, optionally with one or more dispersing agents, to produce a fine particle suspension of the compound. One or more wetting agents may be included in the composition and a suspending agent may be included to reduce the rate at which the particles settle. Alternatively, the active ingredient may be dry milled and added to water, containing agents hereinbefore described, to produce the desired end product.

Aerosol formulations comprise the active ingredient and a suitable propellant (for example n-butane). Active ingredients may also be dissolved or dispersed in a suitable medium (for example water or a water miscible liquid, such as n-propanol) to provide compositions for use in non-pressurized, hand-actuated spray pumps. The active ingredient may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains the active ingredient and, optionally, a carrier or diluent therefor. The polymeric shell may be produced by either an interfacial polycondensation reaction or by a coacervation procedure. The compositions may provide for controlled release of the compound of the active ingredient. Active ingredients may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of the active ingredient). Such additives include surface active agents, spray additives based on oils, for example certain mineral oils, natural plant oils (such as soy bean and rape seed oil) and/or modified plant oils (e.g. esterified plant oils), and blends of these with other bio-enhancing adjuvants (ingredients which may aid or modify the action of the active ingredient. Where the active ingredient described herein is employed in methods of protecting crops of useful plants, methods of enhancing/maintaining yield and/or methods of increasing/maintaining pollination in crops of useful plants, it is preferred that said active ingredient (or compositions containing such active ingredient) is applied to the crop of useful plants at the flower-bud stage. In particular for crops of useful plants wherein said plants have yellow flowers, (e.g. oilseed rape, mustard etc.) it is preferred that the application occurs at the green to yellow bud stage.

In some embodiments, the acceptable agricultural carrier is a transgenic organism expressing an interfering RNA of the invention. In some embodiments the transgenic organism may be a transgenic plant expressing the interfering RNA of the invention that when fed upon by a target coleopteran and/or hemipteran plant pest causes the target coleopteran and/or hemipteran plant pest to stop feeding, growing or reproducing or causing death of the target coleopteran and/or hemipteran plant pest. In some embodiments the plant pest is selected from the group consisting of *Sitophilus oryzae* (So; rice weevil), *Diabrotica virgifera virgifera* (Dv; western corn rootworm), *Diabrotica undecimpunctata howardi* (Du; southern corn rootworm), *Diabrotica barberi* (db; northern corn rootworm), *Phyllotreta armoraciae* (Pa; horseradish flea beetle), *Phyllotreta nemorum* (Pn; turnip flea beetle), *Phyllotreta cruciferae* (Pu; crucifer flea beetle), *Phyllotreta striolata* (Ps; striped flea beetle), *Phyllotreta atra* (Pt; flea beetle), *Psylliodes chrysocephala* (Pc; cabbage-stem flea beetle), *Meligethes aeneus* (Ma; pollen beetle), *Ceutorhynchus assimilis* (Ca; cabbage seedpod weevil), *Leptinotarsa decemlineata* (Ld; Colorado potato beetle), and/or the hemipteran insect pest is selected from the group consisting of *Nezara viridula* (Nv; green stink bug), *Euschistus heros* (Eh; brown stink bug), and *Piezodorus guildinii* (Pg; red-banded stink bug).

In other embodiments, the transgenic plant is a transgenic corn plant and the target pest is a *Diabrotica* insect pest. In still other embodiments, the *Diabrotica* insect pest is selected from the group consisting of *Diabrotica virgifera virgifera* (Dv; western corn rootworm), *Diabrotica undecimpunctata howardi* (Du; southern corn rootworm), and *Diabrotica barberi* (db; northern corn rootworm).

In other embodiments, the transgenic organism is selected from, but not limited to, the group consisting of: yeast, fungi, algae, bacteria, virus or an arthropod expressing the interfering RNA molecule of the invention. In some embodiments, the transgenic organism is a virus, for example an insect baculovirus that expresses an interfering RNA molecule of the invention upon infection of an insect host. Such a baculovirus is likely more virulent against the target insect than the wildtype untransformed baculovirus. In other embodiments the transgenic organism is a transgenic bacterium that is applied to an environment where a target pest occurs or is known to have occurred. In some embodiments, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive interfering RNA molecule for the same purpose.

In some embodiments, the invention encompasses transgenic plants, or parts thereof, comprising an interfering RNA molecule, a nucleic acid construct, a chimeric nucleic acid molecule, an artificial plant microRNA precursor molecule and/or a composition of the invention, wherein the transgenic plant has enhanced resistance to a coleopteran insect, hemipteran insect, or *Diabrotica* insect as compared to a control plant (e.g., a plant not comprising the interfering RNA molecule, the dsRNA, the nucleic acid molecule, the nucleic acid construct, the chimeric nucleic acid molecule, the artificial plant microRNA precursor molecule and/or the composition of the invention). In other embodiments, the transgenic plant, or part thereof, is a transgenic corn plant, or part thereof. The invention further encompasses transgenic seed of the transgenic plants of the invention, wherein the transgenic seed comprises an interfering RNA molecule, a nucleic acid construct, a chimeric nucleic acid molecule, an artificial plant microRNA precursor molecule and/or a composition of the invention. In some embodiments the transgenic seed is a transgenic corn seed.

Transgenic plants expressing an interfering RNA of the invention are tolerant or resistant to attack by target insect pests. When the insect starts feeding on such a transgenic plant, it also ingests the expressed dsRNA or siRNA. This may deter the insect from further biting into the plant tissue or may even harm or kill the insect. A nucleic acid sequence encoding a dsRNA or siRNA of the invention is inserted into an expression cassette, which is then preferably stably integrated in the genome of the plant. The nucleic acid sequences of the expression cassette introduced into the genome of the plant are heterologous to the plant and non-naturally occurring. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, *papaya*, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees. In further embodiments, the transgenic plant is a transgenic corn plant.

Expression of the interfering RNA molecule in transgenic plants is driven by regulatory sequences comprising promoters that function in plants. The choice of promoter will vary depending on the temporal and spatial requirements for expression, and also depending on the insect target species. Thus, expression of the interfering RNAs of this invention in leaves, in stalks or stems, in ears, in inflorescences (e.g. spikes, panicles, cobs, etc.), in roots, and/or seedlings is contemplated. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the dsRNA or siRNA in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

In some embodiments, tissue-specific/tissue-preferred promoters can be used. Tissue-specific or tissue-preferred expression patterns include, but are not limited to, green tissue specific or preferred, root specific or preferred, stem specific or preferred, and flower specific or preferred. In addition, promoters functional in plastids can be used. In some embodiments of the invention, inducible promoters can be used. In further aspects, the nucleotide sequences of the invention can be operably associated with a promoter that is wound inducible or inducible by pest or pathogen infection (e.g., an insect or nematode plant pest)

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

In some embodiments, a recombinant nucleic acid molecule of the invention can be an "expression cassette." As used herein, "expression cassette" means a recombinant nucleic acid molecule comprising a nucleotide sequence of interest (e.g., the nucleotide sequences of the invention), wherein the nucleotide sequence is operably associated with at least a control sequence (e.g., a promoter). Thus, some embodiments of the invention provide expression cassettes designed to express nucleotides sequences encoding the dsRNAs or siRNAs of the invention. In this manner, for example, one or more plant promoters operably associated with one or more nucleotide sequences of the invention are provided in expression cassettes for expression in a corn plant, plant part and/or plant cell.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tm1 terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

An expression cassette of the invention also can include polynucleotides that encode other desired traits. Such desired traits can be other polynucleotides which confer insect resistance, or which confer nematode resistance, or other agriculturally desirable traits. Such polynucleotides can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a single transgene can comprise multiple expression cassettes, such that multiple expression cassettes are introduced into the genome of a transformed cell at a single genomic location. Alternatively, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

Thus, an expression cassette can include a coding sequence for one or more polypeptides for agronomic traits that primarily are of benefit to a seed company, grower or grain processor. A polypeptide of interest can be any polypeptide encoded by a polynucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construct of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors of the invention may also comprise other selectable marker genes, for example, phosphomannose isomerase (pmi), which provides for positive selection of the transgenic plants as disclosed in U.S. Pat. Nos. 5,767,378 and 5,994,629, herein incorporated by reference, or phosphinotricin acetyltransferase (pat), which provides tolerance to the herbicide phosphinotricin (glufosinate). The choice of selectable marker is not, however, critical to the invention.

In other embodiments, a nucleic acid sequence of the invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Transgenic plants or seed comprising an interfering RNA of the invention can also be treated with an insecticide or insecticidal seed coating as described in U.S. Pat. Nos. 5,849,320 and 5,876,739, herein incorporated by reference. Where both the insecticide or insecticidal seed coating and the transgenic plant or seed of the invention are active against the same target insect, for example a coleopteran pest, a hemipteran pest or a *Diabrotica* target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a coleopteran insect population, a hemipteran insect population, or a *Diabrotica* insect population comprising providing a transgenic plant or seed of the invention and applying to the plant or the seed an insecticide or insecticidal seed coating to a transgenic plant or seed of the invention. Examples of such insecticides and/or insecticidal seed coatings include, without limitation, a carbamate, a pyrethroid, an organophosphate, a fiprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, FURADAN® (carbofuran), LANATE® (methomyl, metomil, mesomile), SEVIN® (carbaryl), TALSTAR® (bifenthrin), FORCE® (tefluthrin), AMMO® (cypermethrin), CYMBUSH® (cypermethrin), DELTA GOLD® (deltamethrin), KARATE® (lambda-cyhalothrin), AMBUSH® (permethrin), POUNCE® (permethrin), BRIGADE® (bifenthrin), CAPTURE® (bifenthrin), PROSHIELD® (tefluthrin), WARRIOR® (lambda-cyhalothrin), DURSBAN® (chlorphyrifos), FORTRESS® (chlorethoxyfos), MOCAP® (ethoprop), THIMET® (phorate), AASTAR® (phorate, flucythinate), RAMPART® (phorate), COUNTER® (terbufos), CYGON® (dimethoate), DICAPTHON, REGENT® (fipronil), CRUISER® (thiamethoxam), GAUCHO® (imidacloprid), PRESCRIBE® (imidacloprid), PONCHO® (clothianidin) and AZTEC® (cyfluthrin, tebupirimphos).

The compositions of the invention can also be combined with other biological control agents to enhance control of a coleopteran insect, a hemipteran insect, or a *Diabrotica* insect population. Thus, the invention provides a method of enhancing control of a coleopteran insect population, hemipteran insect population, or a *Diabrotica* insect population by providing a transgenic plant that produces an interfering RNA of the invention and further comprises a polynucleotide that encodes a second insecticidal agent. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the transgenic plant may produce an interfering RNA of the invention and a second insecticidal agent which is derived from sources other than *B. thuringiensis*. The second insecticidal agent can be an agent selected from the group comprising a patatin, a protease, a protease inhibitor, a chitinase, a urease, an alpha-amylase inhibitor, a pore-forming protein, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphearicus* insecticidal protein, a *Chromobacterium* spp. insecticidal protein, a *Yersinia entomophaga* insecticidal protein, a *Paenibacillus popiliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia*, or *Yersinia*. In other embodiments, the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from L *sphaericus*. In still other embodiments, the insecticidal protein may be engineered or may be a hybrid or chimera of any of the preceding insecticidal proteins.

In another embodiment, the transgenic plant and transgenic seed is a corn plant or corn seed. In another embodiment, the transgenic corn plant is provided by crossing a first transgenic corn plant comprising a dsRNA of the invention with a transgenic corn plant comprising a transgenic event selected from the group consisting of MIR604, Event 5307, DAS51922-7, MON863 and MON88017.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to the transgenic plant or seed of the invention, which has activity against coleopteran insects, the treated plant or coated transgenic seed controls both lepidopteran and coleopteran insect pests.

In further embodiments, the invention encompasses a biological sample from a transgenic plant, seed, or parts thereof, of the invention, wherein the sample comprises a nucleic acid that is or encodes at least one strand of a dsRNA of the invention. In other embodiments, the invention encompasses a commodity product derived from a transgenic plant, seed, or parts thereof, of the invention. In some embodiments, the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants. In other embodiments, the biological sample or commodity product is toxic to insects. In other embodiments, the transgenic plant is a transgenic corn plant.

The invention further encompasses a method of controlling a coleopteran and/or hemipteran pest insect comprising contacting the insect with a nucleic acid molecule that is or is capable of producing an interfering RNA molecule of the invention for inhibiting expression of a target gene in the insect thereby controlling the coleopteran and/or hemipteran insect. In some embodiments, the target gene comprises a coding sequence (i) having at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:1-1814, or a complement thereof; (ii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one SEQ ID NOs:1-1814, or a complement thereof; (iii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of a nucleotide sequence encoding an amino acid sequence encoded by any one of SEQ ID NOs:1-1814, or a complement thereof. In some embodiments the target gene coding sequence comprises any one of SEQ ID NOs:1-1814, or a complement thereof, or (iv) can hybridize under stringent conditions to a polynucleotide selected from the group consisting of any one of SEQ ID NOs:1-1814, and the complements thereof. In other embodiments, the interfering RNA molecule of the invention is complementary to a portion of a mRNA polynucleotide transcribable from the pest insect target genes described herein.

In some embodiments of the method of controlling a coleopteran and/or hemipteran insect pest, the interfering RNA molecule of the invention comprises at least one dsRNA, wherein the dsRNA is a region of double-stranded RNA comprising annealed complementary strands, one strand of which comprises a sequence of at least 19 consecutive nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:3629-7256, or the complement thereof; or (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:3629-7256, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of a nucleotide sequence encoding an amino acid sequence encoded by any one of SEQ ID NOs:3629-7256, or the complement thereof, or (iv) can hybridize under stringent conditions to a polynucleotide selected from the group consisting of any one of SEQ ID NOs:3629-7256, and the complements thereof.

In some embodiments of the method of controlling a coleopteran and/or hemipteran pest insect, the pest insect is selected from the group consisting of *Sitophilus oryzae* (So; rice weevil), *Diabrotica virgifera virgifera* (Dv; western corn rootworm), *Diabrotica undecimpunctata howardi* (Du; southern corn rootworm), *Diabrotica barberi* (db; northern corn rootworm), *Phyllotreta armoraciae* (Pa; horseradish flea beetle), *Phyllotreta nemorum* (Pn; turnip flea beetle), *Phyllotreta cruciferae* (Pu; crucifer flea beetle), *Phyllotreta striolata* (Ps; striped flea beetle), *Phyllotreta atra* (Pt; flea beetle), *Psylliodes chrysocephala* (Pc; cabbage-stem flea beetle), *Meligethes aeneus* (Ma; pollen beetle), *Ceutorhynchus assimilis* (Ca; cabbage seedpod weevil), *Leptinotarsa decemlineata* (Ld; Colorado potato beetle), and/or the hemipteran insect pest is selected from the group consisting of *Nezara viridula* (Nv; green stink bug), *Euschistus heros* (Eh; brown stink bug), and *Piezodorus guildinii* (Pg; red-banded stink bug).

In other embodiments of the method of controlling a coleopteran and/or hemipteran pest insect, the contacting comprises (a) planting a transgenic seed capable of producing a transgenic plant that expresses the nucleic acid molecule, wherein the insect feeds on the transgenic plant, or part thereof; or (b) applying a composition comprising the nucleic acid molecule to a seed or plant, or part thereof, wherein the insect feeds on the seed, the plant, or a part thereof. In some embodiments, the transgenic seed and the transgenic plant is a corn seed or a corn plant. In other embodiments the seed or plant is a corn seed or a corn plant.

The invention also encompasses a method of controlling a *Diabrotica* insect comprising contacting the *Diabrotica* insect with a nucleic acid molecule that is or is capable of producing the interfering RNA molecule of the invention for inhibiting expression of a target gene in the *Diabrotica* insect, and also contacting the *Diabrotica* insect with at least a second insecticidal agent for controlling *Diabrotica*, wherein said second insecticidal agent comprises a *B. thuringiensis* insecticidal protein, thereby controlling the *Diabrotica* insect. The invention also encompasses a method for controlling *Diabrotica* insect pests on a plant, comprising topically applying to said plant a pesticide composition comprising an interfering RNA of the invention and at least a second insecticidal agent for controlling *Diabrotica*, wherein said second insecticidal agent does not comprise a *B. thuringiensis* insecticidal protein, and providing said plant in the diet of said *Diabrotica* insect. The invention also encompasses a method wherein the second insecticidal agent comprises a patatin, a protease, a protease inhibitor, a urease, an alpha-amylase inhibitor, a pore-forming protein, a lectin, an engineered antibody or antibody fragment, or a chitinase. The second insecticidal agent may also be a *Bacillus cereus* insecticidal protein, a *Xenorhabdus* spp. insecticidal protein, a *Photorhabdus* spp. insecticidal protein, a *Brevibacillus laterosporous* insecticidal protein, a *Lysinibacillus sphearicus* insecticidal protein, a *Chromobacterium* ssp. insecticidal protein, a *Yersinia entomophaga* insecticidal protein, a *Paenibacillus popiliae* insecticidal protein, or a *Clostridium* spp. insecticidal protein.

The invention also encompasses a method of reducing an adult coleopteran insect population or an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA molecule of the invention capable of inhibiting expression of a target gene as described herein in an adult insect, thereby reducing the adult coleopteran insect population or adult *Diabrotica* insect population.

In some embodiments, the invention encompasses a method of reducing the level of a target mRNA transcribable from a target gene as described herein in a coleopteran insect, a hemipteran insect or a *Diabrotica* insect comprising contacting the insect with a composition comprising the interfering RNA molecule of the invention, wherein the interfering RNA molecule reduces the level of the target mRNA in a cell of the insect. In some embodiments, the interfering RNA of the method comprises at least one dsRNA, wherein the dsRNA is a region of double-stranded RNA comprising annealed complementary strands, one strand of which comprises a sequence of at least 19 consecutive nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:3629-7256, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:3629-7256, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of a nucleotide sequence encoding an amino acid sequence encoded by any one of SEQ ID NOs:3629-7256, or the complement thereof, or (iv) can hybridize under stringent conditions to a polynucleotide selected from the group consisting of any one of SEQ ID NOs:3629-7256, and the complements thereof, wherein the interfering RNA molecule has insecticidal activity against the target coleopteran insect, the target hemipteran insect or the target *Diabrotica* insect. In another embodiment, the contacting is achieved by the target insect feeding on the composition. In other embodiments, production of the protein encoded by the target mRNA is reduced. In other embodiments, the target protein comprises an amino acid having at least about 80%, at least about 85%, at least about 90%, at least about 91%, at least about 92%, at least about 93%, at least about 94%, at least about 95%, at least about 96%, at least about 97%, at least about 98% or at least about 99% identity to any one SEQ ID NOs:10885-12698. In other embodiments the target protein comprises any one SEQ ID NOs:10885-12698. In other embodiments, the interfering RNA is contacted with a coleopteran and/or hemipteran insect or a *Diabrotica* insect through a transgenic organism expressing the interfering RNA. In other embodiments, the transgenic organism is a transgenic plant, a transgenic microorganism, a transgenic bacterium or a transgenic endophyte. In other embodiments, the interfering RNA is contacted with a coleopteran and/or hemipteran insect or a *Diabrotica* insect by topically applying an interfering RNA in an acceptable agricultural carrier to a plant or plant part on which the insect feeds. In some embodiments, the interfering RNA that reduces the level of a target mRNA transcribable from a target gene described herein is lethal to the coleopteran and/or hemipteran insect or *Diabrotica* insect. In some embodiments, the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle) and *D. virgifera zeae* (Mexican corn rootworm).

In some embodiments, the invention encompasses a method of conferring coleopteran and/or hemipteran insect tolerance or *Diabrotica* insect tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, wherein the dsRNA molecule, nucleic acid construct, chimeric nucleic acid molecule, artificial plant microRNA precursor molecule and/or composition of the invention are toxic to the insect, thereby conferring tolerance of the plant or part thereof to the coleopteran insect and/or hemipteran insect or *Diabrotica* insect. In other embodiments, the introducing step is performed by transforming a plant cell and producing the transgenic plant from the transformed plant cell. In still other embodiments, the introducing step is performed by breeding two plants together.

In other embodiments, the invention encompasses a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, wherein the dsRNA, nucleic acid molecule, nucleic acid construct, chimeric nucleic acid molecule, artificial plant microRNA precursor molecule and/or composition of the invention are toxic to the *Diabrotica* insect, thereby reducing root damage to the plant. In other embodiments, the introducing step is performed by transforming a plant cell and producing the transgenic plant from the transformed plant cell. In still other embodiments, the introducing step is performed by breeding two plants together.

In still other embodiments, the invention encompasses a method of producing a transgenic plant cell having toxicity to a coleopteran insect and/or hemipteran insect or *Diabrotica* insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the insect compared to a control plant cell (e.g., a plant cell not comprising the interfering RNA molecule, the dsRNA, the nucleic acid molecule, the nucleic acid construct, the chimeric nucleic acid molecule, the artificial plant microRNA precursor molecule and/or the composition of the invention). In some embodiments, the invention encompasses a plurality of transgenic plant cells produced by this method. In other embodiments, the plurality of transgenic plant cells is grown under conditions which include natural sunlight. In other embodiments, the introducing step is performed by transforming a plant cell and producing the transgenic plant from the transformed plant cell. In still other embodiments, the introducing step is performed by breeding two plants together.

In some embodiments, the invention encompasses a method of producing a transgenic plant having enhanced tolerance to coleopteran and/or hemipteran or *Diabrotica* insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to coleopteran or *Diabrotica* insect feeding damage compared to a control plant (e.g., a plant not comprising the interfering RNA molecule, the dsRNA, the nucleic acid molecule, the nucleic acid construct, the chimeric nucleic acid molecule, the artificial plant microRNA precursor molecule and/or the composition of the invention). In other embodiments, the introducing step is performed by transforming a plant cell and producing the transgenic plant from the transformed plant cell. In still other embodiments, the introducing step is performed by breeding two plants together.

In some embodiments, the invention encompasses a method of providing a corn grower with a means of controlling a coleopteran and/or hemipteran insect pest population or a *Diabrotica* insect pest population in a corn crop comprising (a) selling or providing to the grower transgenic corn seed that comprises an interfering RNA, a nucleic acid molecule, a nucleic acid construct, a chimeric nucleic acid molecule, an artificial plant microRNA precursor molecule and/or a composition of the invention; and (b) advertising to the grower that the transgenic corn seed produce transgenic corn plants that control a coleopteran or *Diabrotica* pest population.

In some embodiments, the invention encompasses a method of identifying a target gene for using as a RNAi strategy for the control of a plant pest for RNAi in a coleopteran and/or hemipteran plant pest, said method comprising the steps of a) producing a primer pair with sequences selected from the group comprising or consisting of SEQ ID NOs:7257-10884, or a complement thereof; b) amplifying an orthologous target from a nucleic acid sample of the plant pest; c) identifying a sequence of an orthologous target gene; d) producing an interfering RNA molecule, wherein the RNA comprises at least one dsRNA, wherein the dsRNA is a region of double-stranded RNA comprising annealed complementary strands, one strand of which comprises a sequence of at least 19 consecutive nucleotides which is at least partially complementary to a target nucleotide sequence within a coleopteran target gene, is obtained; and e) determining if the interfering RNA molecule has insecticidal activity on the plant pest. If the interfering RNA has insecticidal activity on the coleopteran and/or hemipteran pest, a target gene for using in the control of the plant pest has been identified. In some embodiments, the plant pest is a coleopteran and/or hemipteran plant pest.

EXAMPLES

The invention will be further described by reference to the following detailed examples. These examples are provided for the purposes of illustration only, and are not intended to be limiting unless otherwise specified.

Example 1. Identification of Potential RNAi Lethal Genes in Sitophilus oryzae

This example describes the RNA sequencing, the dsRNA synthesis and the testing of all protein coding genes for RNAi induced lethality in a grain pest insect, Sitophilus oryzae (rice weevil).

1.1. RNA Sequencing and Transcriptome Generation of Sitophilus oryzae.

Total RNA was extracted from several Sitophilus oryzae adults, which were species-confirmed by COI barcoding. A whole-body adult Sitophilus oryzae transcriptome was generated by pair-end sequencing on an Illuma HiSeq X (Illumina, Inc., San Diego, CA), essentially according to the manufacturer's instructions. The resulting raw reads (i.e., short fragments of nucleic acid sequence) were de novo assembled using a set of three transcriptome assemblers (Trinity, Velvet/OASES and SOAPdenovo-Trans) to maximize diversity and completeness of the transcriptome. Redundancy in the assembly was reduced using the Evidential Gene pipeline (Genome Informatics Lab, Indiana University), which includes a coding sequence prediction step on the resulting transcripts. From this analysis, 13,509 coding sequences were identified, of which 9,650 (71%) were mapped to a Drosophila ortholog and 11,286 (84%) have at least one form of functional annotation.

1.2. dsRNA Synthesis of all Protein Coding Genes from Sitophilus oryzae dsRNAs of the 13,509 gene targets were produced on an 96 well library synthesis platform. All the dsRNA samples were designed automatically using Primer3 (Untergasser, A., et al. Nucleic Acids Research 40(15):115), a primer design tool, to synthetize a dsRNA fragment of around 500-800 bp based on the coding sequence of each protein coding gene. Smaller fragments were designed if the size of the coding sequence did not allow a 500 bp fragment. Each 96-well plate also contained three negative controls (dsRNA against a Green Fluorescent Protein—GFP) and a positive control (dsRNA against a ubiquitin protein of Sitophilus oryzae).

1.3. Primary Screen of dsRNA Samples for Activity Against Sitophilus oryzae

The dsRNA molecules described above were tested for toxicity against S. oryzae in laboratory bioassays. Bioassays were performed using an RNA-treated artificial diet method. Briefly, 96-well plates of synthesized dsRNA molecules were diluted in a flour suspension. The suspension was divided over 7 replicate 96-well plates and allowed to dry overnight in an oven set at 60° C. One insect was added to each well to have 7 adults per treatment. The plates were maintained at approximately 25° C. and 16/8 light:dark photoperiod. Mortality was recorded at different days post-infestation, with the final survival percentage calculated at 14 or 15 days with Abbott's correction for natural mortality (See for example, Abbott, W. S. J. Am. Mosquito Control Assoc. 3(2):302-303). dsRNA designed to target green fluorescent protein (GFP) was used as a negative control and dsRNA designed to target an ubiquitin protein of S. oryzae was used as a positive control. Results, shown in Table 1, demonstrate that 116 genes (SEQ ID NOs:1-116) in Sitophilus oryzae, when targeted by dsRNA are insecticidal to *Sitophilus oryzae*.

For Tables 1-7, the target gene is named as well as the Target ID. The "SEQ ID NO:" in Tables 1-7 indicates the RNA sequence of the sense strand of the dsRNA tested. "Survival %" is the final survival percentage calculated, with Abbott correction, for each insect bioassay.

TABLE 1

Activity of dsRNA against rice weevil

| Target ID | SEQ ID NO for Target | Putative gene name | Putative Flybase ID | SEQ ID NO: (RNA fragment) | Primary screen Percent Mortality (Abbott corr.) | Confirmation assay Percent Mortality (Abbott corr.) |
|---|---|---|---|---|---|---|
| Gene00101 | 1 | cactin | CG1676 | 3629 | 79 | 26 |
| Gene00111 | 2 | CstF64 | CG7697 | 3630 | 74.8 | 100 |
| Gene00116 | 3 | Rpt4 | CG3455 | 3631 | 100 | 100 |
| Gene00120 | 4 | Prosalpha3 | CG9327 | 3632 | 100 | 100 |
| Gene00129 | 5 | Rpn1 | CG7762 | 3633 | 100 | 100 |
| Gene00132 | 6 | pnr | CG10278 | 3634 | 100 | 100 |
| Gene00134 | 7 | garz | CG8487 | 3635 | 100 | 100 |
| Gene00140 | 8 | Prosbeta3 | CG11981 | 3636 | 100 | 100 |
| Gene00143 | 9 | Trn-SR | CG2848 | 3637 | 74.8 | 0 |
| Gene00161 | 10 | Bap60 | CG4303 | 3638 | 79 | 47 |
| Gene00171 | 11 | l(1)10Bb | CG1639 | 3639 | 100 | 8 |
| Gene00180 | 12 | Pop2 | CG5684 | 3640 | 74.8 | 5 |
| Gene00183 | 13 | CG7483 | CG7483 | 3641 | 100 | 89 |
| Gene00187 | 14 | CCT4 | CG5525 | 3642 | 79 | 89 |
| Gene00190 | 15 | Rpt3 | CG16916 | 3643 | 100 | 100 |
| Gene00191 | 16 | SkpA | CG16983 | 3644 | 79 | 47 |
| Gene00196 | 17 | mts | CG7109 | 3645 | 100 | 100 |
| Gene00213 | 18 | Ubi-p63E | CG11624 | 3646 | 100 | 100 |
| Gene00220 | 19 | CCT7 | CG8351 | 3647 | 100 | 100 |
| Gene00228 | 20 | Dhc64C | CG7507 | 3648 | 82 | 37 |
| Gene00233 | 21 | l(2)37Cb | CG10689 | 3649 | 100 | 65 |
| Gene00236 | 22 | pont | CG4003 | 3650 | 82 | 100 |
| Gene00237 | 23 | Cpsf100 | CG1957 | 3651 | 100 | 100 |
| Gene00238 | 24 | Sf3a1 | CG16941 | 3652 | 100 | 100 |
| Gene00242 | 25 | Rpn8 | CG3416 | 3653 | 100 | 100 |
| Gene00245 | 26 | CCT3 | CG8977 | 3654 | 79 | 100 |
| Gene00266 | 27 | Prosbeta6 | CG4097 | 3655 | 100 | 100 |

TABLE 1-continued Activity of dsRNA against rice weevil

| Target ID | SEQ ID NO for Target | Putative gene name | Putative Flybase ID | SEQ ID NO: (RNA fragment) | Primary screen Percent Mortality (Abbott corr.) | Confirmation assay Percent Mortality (Abbott corr.) |
|---|---|---|---|---|---|---|
| Gene00268 | 28 | Ufd1-like | CG6233 | 3656 | 100 | 75 |
| Gene00269 | 29 | CCT5 | CG8439 | 3657 | 82 | 68 |
| Gene00276 | 30 | Roc1a | CG16982 | 3658 | 82 | 68 |
| Gene00277 | 31 | CCT2 | CG7033 | 3659 | 82 | 100 |
| Gene00281 | 32 | Prosalpha6 | CG4904 | 3660 | 100 | 100 |
| Gene00282 | 33 | fand | CG6197 | 3661 | 100 | 58 |
| Gene00283 | 34 | Spx | CG3780 | 3662 | 64 | 47 |
| Gene00284 | 35 | RpL8 | CG1263 | 3663 | 100 | 68 |
| Gene00286 | 36 | His3:CG31613 | CG31613 | 3664 | 100 | 68 |
| Gene00289 | 37 | CCT6 | CG8231 | 3665 | 100 | 79 |
| Gene00305 | 38 | Uba1 | CG1782 | 3666 | 100 | 68 |
| Gene00306 | 39 | Hel25E | CG7269 | 3667 | 100 | 100 |
| Gene00309 | 40 | Rpn3 | CG42641 | 3668 | 100 | 100 |
| Gene00313 | 41 | Slu7 | CG1420 | 3669 | 100 | 100 |
| Gene00323 | 42 | RpS8 | CG7808 | 3670 | 79 | 100 |
| Gene00325 | 43 | Rpn11 | CG18174 | 3671 | 100 | 100 |
| Gene00337 | 44 | Rpt6 | CG1489 | 3672 | 100 | 100 |
| Gene00340 | 45 | Ykt6 | CG1515 | 3673 | 100 | 100 |
| Gene00343 | 46 | Prosalpha5 | CG10938 | 3674 | 100 | 100 |
| Gene00356 | 47 | Vha44 | CG8048 | 3675 | 82 | 8 |
| Gene00367 | 48 | CCT1 | CG5374 | 3676 | 100 | 100 |
| Gene00368 | 49 | Prosbeta7 | CG12000 | 3677 | 100 | 88 |
| Gene00370 | 50 | Exo84 | CG6095 | 3678 | 100 | 68 |
| Gene00379 | 51 | pea | CG8241 | 3679 | 100 | 100 |
| Gene00384 | 52 | CG9175 | CG9175 | 3680 | 100 | 100 |
| Gene00416 | 53 | Rpn6 | CG10149 | 3681 | 100 | 100 |
| Gene00418 | 54 | Lam | CG6944 | 3682 | 100 | 100 |
| Gene00424 | 55 | TER94 | CG2331 | 3683 | 100 | 89 |
| Gene00428 | 56 | cpb | CG17158 | 3684 | 100 | 68 |
| Gene00429 | 57 | fs(1)h | CG2252 | 3685 | 82 | 42 |
| Gene00532 | 58 | RpL4 | CG5502 | 3686 | 82 | 88 |
| Gene00544 | 59 | Spt6 | CG12225 | 3687 | 100 | 100 |
| Gene00557 | 60 | ncm | CG12750 | 3688 | 100 | 100 |
| Gene00892 | 61 | Rop | CG15811 | 3689 | 100 | 100 |
| Gene00949 | 62 | Sec10 | CG6159 | 3690 | 82.9 | 100 |
| Gene01074 | 63 | Sf3a2 | CG10754 | 3691 | 65.8 | 90 |
| Gene01187 | 64 | SmD3 | CG8427 | 3692 | 81.1 | 100 |
| Gene01510 | 65 | UQCR-C2 | CG4169 | 3693 | 83.8 | 100 |
| Gene01576 | 66 | Bet1 | CG14084 | 3694 | 100 | 83 |
| Gene01649 | 67 | Vha55 | CG17369 | 3695 | 100 | 100 |
| Gene01735 | 68 | CG15862 | CG15862 | 3696 | 65.7 | 0 |
| Gene01896 | 69 | arm | CG11579 | 3697 | 82.8 | 100 |
| Gene02220 | 70 | CG9667 | CG9667 | 3698 | 65.7 | 100 |
| Gene02411 | 71 | Ran | CG1404 | 3699 | 100 | 100 |
| Gene02760 | 72 | Ssk | CG6981 | 3700 | 100 | 100 |
| Gene02775 | 73 | Cdc5 | CG6905 | 3701 | 100 | 75 |
| Gene03652 | 74 | AP-1sigma | CG5864 | 3702 | 100 | 100 |
| Gene03841 | 75 | CG11779 | CG11779 | 3703 | 67.6 | 83 |
| Gene04283 | 76 | CG1542 | CG1542 | 3704 | 63 | 0 |
| Gene04844 | 77 | pea | CG8241 | 3705 | 100 | 91 |
| Gene05081 | 78 | pAbp | CG5119 | 3706 | 100 | 100 |
| Gene05129 | 79 | AP-1-2beta | CG12532 | 3707 | 100 | 100 |
| Gene05740 | 80 | RpL12 | CG3195 | 3708 | 100 | 100 |
| Gene06225 | 81 | CG1129 | CG1129 | 3709 | 100 | 100 |
| Gene06978 | 82 | cpa | CG10540 | 3710 | 63.1 | 75 |
| Gene08627 | 83 | mesh | CG31004 | 3711 | 100 | 100 |
| Gene08840 | 84 | RpLP2 | CG4918 | 3712 | 100 | 90 |
| Gene08867 | 85 | alpha-Cat | CG17947 | 3713 | 100 | 100 |
| Gene08949 | 86 | Nup62 | CG6251 | 3714 | 80.6 | 90 |
| Gene09268 | 87 | Sar1 | CG7073 | 3715 | 100 | 100 |
| Gene09411 | 88 | DCTN3-p24 | CG9893 | 3716 | 80.6 | 31 |
| Gene09812 | 89 | Sac1 | CG9128 | 3717 | 80.6 | 90 |
| Gene09966 | 90 | atms | CG2503 | 3718 | 80.6 | 100 |
| Gene10001 | 91 | Rpn7 | CG5378 | 3719 | 100 | 100 |
| Gene10086 | 92 | Lpt | CG5591 | 3720 | 80.6 | 1 |
| Gene10142 | 93 | DNApol-alpha180 | CG6349 | 3721 | 68.4 | 70 |
| Gene10189 | 94 | rept | CG9750 | 3722 | 100 | 100 |
| Gene10549 | 95 | Snr1 | CG1064 | 3723 | 68.4 | 41 |
| Gene10649 | 96 | Rho1 | CG8416 | 3724 | 100 | 100 |
| Gene10683 | 97 | Nup154 | CG4579 | 3725 | 68.4 | 50 |
| Gene10692 | 98 | Nup160 | CG4738 | 3726 | 68.4 | 80 |

TABLE 1-continued

Activity of dsRNA against rice weevil

| Target ID | SEQ ID NO for Target | Putative gene name | Putative Flybase ID | SEQ ID NO: (RNA fragment) | Primary screen Percent Mortality (Abbott corr.) | Confirmation assay Percent Mortality (Abbott corr.) |
|---|---|---|---|---|---|---|
| Gene10724 | 99 | Cse1 | CG13281 | 3727 | 84.2 | 70 |
| Gene10755 | 100 | asf1 | CG9383 | 3728 | 100 | 100 |
| Gene11048 | 101 | Tbp | CG9874 | 3729 | 84.2 | 80 |
| Gene11055 | 102 | ATPsyndelta | CG2968 | 3730 | 100 | 100 |
| Gene11554 | 103 | nudC | CG9710 | 3731 | 84.2 | 70 |
| Gene11636 | 104 | Srp19 | CG4457 | 3732 | 64.3 | 100 |
| Gene11792 | 105 | crn | CG3193 | 3733 | 64.3 | 100 |
| Gene12327 | 106 | Sec61alpha | CG9539 | 3734 | 100 | 100 |
| Gene12548 | 107 | Cbp20 | CG12357 | 3735 | 100 | 100 |
| Gene12739 | 108 | Cyt-c1 | CG4769 | 3736 | 100 | 100 |
| Gene12888 | 109 | CG6015 | CG6015 | 3737 | 82.1 | 100 |
| Gene13224 | 110 | RpL7A | CG3314 | 3738 | 100 | 100 |
| Gene13823 | 111 | betaggt-II | CG18627 | 3739 | 68.2 | 100 |
| Gene13837 | 112 | Fs(2)Ket | CG2637 | 3740 | 100 | 100 |
| Gene13977 | 113 | noi | CG2925 | 3741 | 100 | 100 |
| Gene14143 | 114 | SmB | CG5352 | 3742 | 82.9 | 100 |
| Gene14302 | 115 | CG43088 | CG43088 | 3743 | 65.8 | 31 |
| Gene14726 | 116 | CG3848 | CG3848 | 3744 | 65.8 | 41 |

1.4. Confirmation Assay of Candidate RNAi Targets in *Sitophilus oryzae*

The dsRNA molecules that gave the highest mortality in the primary screen were re-arrayed in 96-well plates and tested with twelve replicates in the same *Sitophilus oryzae* laboratory bioassay as described above. Results of the confirmation assay can also be found in Table 1.

It has previously been suggested that certain genes of a given insect species can be predicted to confer an RNAi-mediated insecticidal effect based on the essential nature of the gene in insects. However, empirical evaluation of the target genes revealed that the insecticidal effect could not be predicted (See, for example, Baum et al., 2007, Nature Biotechnology 25: 1322-1326; also U.S. Patent Publication No. 2015/0322456). Additionally, it has been suggested that a gene which has been shown to be a useful target for RNAi-mediated insect control for one insect pest may be a useful target for RNAi-mediated insect control of a second insect pest of a different genus and/or family. However, empirical evaluation of the target gene in different insect pests of different families show that a given target with very high insecticidal activity in one insect pest may not produce significant mortality or growth inhibition in a second insect pest (Knorr et al, 2018, Scientific Reports 8: 2061, DOI: 10.1038/s41598-018-20416-y). Therefore, the insecticidal activity of a dsRNA molecule against a target gene of an insect pest can only be determined empirically.

Example 2. Identification of Potential RNAi Lethal Target Genes in Corn Rootworm This example describes the testing of dsRNA molecules against target genes in western corn rootworm, *Diabrotica virgifera virgifera* (Dv), southern corn rootworm, *Diabrotica undecimpunctata howardi* (Du), and northern corn rootworm, *Diabrotica barberi* (db), that are orthologues of the *Sitophilus oryzae* target genes described in Table 1.

2.1. RNA Sequencing and Transcriptome Generation of Corn Rootworms.

The corn rootworm transcriptomes were generated in a similar way as described for *Sitophilus oryzae* in Example 1. With BLAST most of the orthologous genes from the *Sitophilus oryzae* positives were identified in the transcriptomes of the different rootworm species; Dv (SEQ ID NOs:117-228), Du (SEQ ID NOs:229-340) and for db (SEQ ID NOs:341-451).

2.2. dsRNA Synthesis from the Candidate Target Genes of Corn Rootworm.

The same 96-well library synthesis platform was used to produce dsRNA samples for testing against corn rootworm. The negative control (dsRNA against a Green Fluorescent Protein—GFP) and the positive control (dsRNA against the species specific ubiquitin protein) were produced in the same manner.

2.3. Testing of dsRNA Samples Against Corn Rootworms.

Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to the appropriate concentration such that 20 µl of solution was added to the surface of the diet in half of the wells of a 48-well plate, with a final overlay concentration of 0.1 µg dsRNA per well. One or two corn rootworm larvae were added to each well to have between 24 and 48 replicate larvae per dsRNA tested. Each 48-well plate was maintained at approximately 26° C. and 16:8 light:dark photoperiod. Mortality was recorded at 7 days after treatment. The results, shown in Table 2, demonstrate that 112 dsRNA molecules having complementarity to 112 target genes, which are orthologues to the initial 116 *Sitophilus* target genes described in Table 1, are highly toxic to *Diabrotica virgifera virgifera* (Dv; western corn rootworm).

TABLE 2

Results of Dv dsRNA primary screen

| Target ID | SEQ ID NO for Target | Putative Gene name | Putative Flybase ID | SEQ ID NO: (RNA fragment) | Percent Mortality (Abbott corr.) |
|---|---|---|---|---|---|
| Gene00101 | 117 | cactin | CG1676 | 3745 | 36.6 |
| Gene00111 | 118 | CstF64 | CG7697 | 3746 | 45.2 |
| Gene00116 | 119 | Rpt4 | CG3455 | 3747 | 60.6 |
| Gene00120 | 120 | Prosalpha3 | CG9327 | 3748 | 48.7 |

TABLE 2-continued

Results of Dv dsRNA primary screen

| Target ID | SEQ ID NO for Target | Putative Gene name | Putative Flybase ID | SEQ ID NO: (RNA fragment) | Percent Mortality (Abbott corr.) |
|---|---|---|---|---|---|
| Gene00129 | 121 | Rpn1 | CG7762 | 3749 | 74.6 |
| Gene00132 | 122 | pnr | CG10278 | 3750 | 86.5 |
| Gene00134 | 123 | garz | CG8487 | 3751 | 32.5 |
| Gene00140 | 124 | Prosbeta3 | CG11981 | 3752 | 68 |
| Gene00143 | 125 | Tm-SR | CG2848 | 3753 | 54.1 |
| Gene00161 | 126 | Bap60 | CG4303 | 3754 | 94.2 |
| Gene00171 | 127 | l(1)10Bb | CG1639 | 3755 | 43 |
| Gene00180 | 128 | Pop2 | CG5684 | 3756 | 79.3 |
| Gene00183 | 129 | CG7483 | CG7483 | 3757 | 44.6 |
| Gene00187 | 130 | CCT4 | CG5525 | 3758 | 50.3 |
| Gene00190 | 131 | Rpt3 | CG16916 | 3759 | 38 |
| Gene00191 | 132 | SkpA | CG16983 | 3760 | 49.8 |
| Gene00196 | 133 | mts | CG7109 | 3761 | 55.6 |
| Gene00213 | 134 | Ubi-p63E | CG11624 | 3762 | 100 |
| Gene00220 | 135 | CCT7 | CG8351 | 3763 | 57.5 |
| Gene00228 | 136 | Dhc64C | CG7507 | 3764 | 90.7 |
| Gene00233 | 137 | l(2)37Cb | CG10689 | 3765 | 30.6 |
| Gene00236 | 138 | pont | CG4003 | 3766 | 83.1 |
| Gene00237 | 139 | Cpsf100 | CG1957 | 3767 | 71.1 |
| Gene00238 | 140 | Sf3a1 | CG16941 | 3768 | 48.9 |
| Gene00242 | 141 | Rpn8 | CG3416 | 3769 | 53.7 |
| Gene00245 | 142 | CCT3 | CG8977 | 3770 | 75.7 |
| Gene00266 | 143 | Prosbeta6 | CG4097 | 3771 | 52.8 |
| Gene00268 | 144 | Ufd1-like | CG6233 | 3772 | 30.2 |
| Gene00269 | 145 | CCT5 | CG8439 | 3773 | 82.2 |
| Gene00276 | 146 | Roc1a | CG16982 | 3774 | 66 |
| Gene00277 | 147 | CCT2 | CG7033 | 3775 | 75.3 |
| Gene00281 | 148 | Prosalpha6 | CG4904 | 3776 | 67.8 |
| Gene00282 | 149 | fand | CG6197 | 3777 | 61.8 |
| Gene00283 | 150 | Spx | CG3780 | 3778 | 61.4 |
| Gene00284 | 151 | RpL8 | CG1263 | 3779 | 66.4 |
| Gene00286 | 152 | His3:CG31613 | CG31613 | 3780 | 82.7 |
| Gene00289 | 153 | CCT6 | CG8231 | 3781 | 82.7 |
| Gene00305 | 154 | Uba1 | CG1782 | 3782 | 45.8 |
| Gene00306 | 155 | Hel25E | CG7269 | 3783 | 75.3 |
| Gene00309 | 156 | Rpn3 | CG42641 | 3784 | 64.2 |
| Gene00313 | 157 | Slu7 | CG1420 | 3785 | 35.5 |
| Gene00323 | 158 | RpS8 | CG7808 | 3786 | 54.2 |
| Gene00325 | 159 | Rpn11 | CG18174 | 3787 | 70.7 |
| Gene00337 | 160 | Rpt6 | CG1489 | 3788 | 71.7 |
| Gene00340 | 161 | Ykt6 | CG1515 | 3789 | 78.5 |
| Gene00343 | 162 | Prosalpha5 | CG10938 | 3790 | 69.8 |
| Gene00367 | 163 | CCT1 | CG5374 | 3791 | 39.4 |
| Gene00368 | 164 | Prosbeta7 | CG12000 | 3792 | 49.4 |
| Gene00370 | 165 | Exo84 | CG6095 | 3793 | 30.3 |
| Gene00379 | 166 | pea | CG8241 | 3794 | 33.6 |
| Gene00384 | 167 | CG9175 | CG9175 | 3795 | 41.1 |
| Gene00416 | 168 | Rpn6 | CG10149 | 3796 | 62.6 |
| Gene00418 | 169 | Lam | CG6944 | 3797 | 39.9 |
| Gene00424 | 170 | TER94 | CG2331 | 3798 | 69.9 |
| Gene00428 | 171 | cpb | CG17158 | 3799 | 38.2 |
| Gene00429 | 172 | fs(1)h | CG2252 | 3800 | 33.4 |
| Gene00532 | 173 | RpL4 | CG5502 | 3801 | 61.9 |
| Gene00544 | 174 | Spt6 | CG12225 | 3802 | 65.8 |
| Gene00557 | 175 | ncm | CG12750 | 3803 | 55.5 |
| Gene00892 | 176 | Rop | CG15811 | 3804 | 70.1 |
| Gene00949 | 177 | Sec10 | CG6159 | 3805 | 57.7 |
| Gene01074 | 178 | Sf3a2 | CG10754 | 3806 | 39.7 |
| Gene01187 | 179 | SmD3 | CG8427 | 3807 | 34.8 |
| Gene01510 | 180 | UQCR-C2 | CG4169 | 3808 | 60.1 |
| Gene01576 | 181 | Bet1 | CG14084 | 3809 | 57.1 |
| Gene01649 | 182 | Vha55 | CG17369 | 3810 | 67.6 |
| Gene01735 | 183 | CG15862 | CG15862 | 3811 | 35.4 |
| Gene01896 | 184 | arm | CG11579 | 3812 | 88.7 |
| Gene02220 | 185 | CG9667 | CG9667 | 3813 | 58 |
| Gene02411 | 186 | Ran | CG1404 | 3814 | 36.7 |
| Gene02775 | 187 | Cdc5 | CG6905 | 3815 | 35.7 |
| Gene03652 | 188 | AP-1sigma | CG5864 | 3816 | 55.1 |
| Gene03841 | 189 | CG11779 | CG11779 | 3817 | 46.1 |
| Gene04283 | 190 | CG1542 | CG1542 | 3818 | 50.4 |
| Gene04844 | 191 | pea | CG8241 | 3819 | 54.3 |
| Gene05081 | 192 | pAbp | CG5119 | 3820 | 62.1 |
| Gene05129 | 193 | AP-1-2beta | CG12532 | 3821 | 75.8 |
| Gene05740 | 194 | RpL12 | CG3195 | 3822 | 67.4 |
| Gene06225 | 195 | CG1129 | CG1129 | 3823 | 91 |
| Gene06978 | 196 | cpa | CG10540 | 3824 | 52.4 |
| Gene08627 | 197 | mesh | CG31004 | 3825 | 100 |
| Gene08840 | 198 | RpLP2 | CG4918 | 3826 | 38.6 |
| Gene08867 | 199 | alpha-Cat | CG17947 | 3827 | 97.4 |
| Gene08949 | 200 | Nup62 | CG6251 | 3828 | 59.6 |
| Gene09268 | 201 | Sar1 | CG7073 | 3829 | 36.3 |
| Gene09411 | 202 | DCTN3-p24 | CG9893 | 3830 | 69.4 |
| Gene09812 | 203 | Sac1 | CG9128 | 3831 | 47.2 |
| Gene09966 | 204 | atms | CG2503 | 3832 | 62.2 |
| Gene10001 | 205 | Rpn7 | CG5378 | 3833 | 39.3 |
| Gene10086 | 206 | Lpt | CG5591 | 3834 | 49.3 |
| Gene10142 | 207 | DNApol-alpha180 | CG6349 | 3835 | 43.1 |
| Gene10549 | 208 | Snrl | CG1064 | 3836 | 35.9 |
| Gene10683 | 209 | Nup154 | CG4579 | 3837 | 36.7 |
| Gene10692 | 210 | Nup160 | CG4738 | 3838 | 36.7 |
| Gene10724 | 211 | Cse1 | CG13281 | 3839 | 43.4 |
| Gene10755 | 212 | asf1 | CG9383 | 3840 | 46.5 |
| Gene11048 | 213 | Tbp | CG9874 | 3841 | 34.3 |
| Gene11055 | 214 | ATPsyndelta | CG2968 | 3842 | 93.5 |
| Gene11554 | 215 | nudC | CG9710 | 3843 | 41.9 |
| Gene11636 | 216 | Srp19 | CG4457 | 3844 | 32.3 |
| Gene11792 | 217 | crn | CG3193 | 3845 | 55.9 |
| Gene12327 | 218 | Sec61alpha | CG9539 | 3846 | 78 |
| Gene12548 | 219 | Cbp20 | CG12357 | 3847 | 50.2 |
| Gene12739 | 220 | Cyt-c1 | CG4769 | 3848 | 57.7 |
| Gene12888 | 221 | CG6015 | CG6015 | 3849 | 40 |
| Gene13224 | 222 | RpL7A | CG3314 | 3850 | 71.7 |
| Gene13823 | 223 | betaggt-II | CG18627 | 3851 | 38.2 |
| Gene13837 | 224 | Fs(2)Ket | CG2637 | 3852 | 45.1 |
| Gene13977 | 225 | noi | CG2925 | 3853 | 38 |
| Gene14143 | 226 | SmB | CG5352 | 3854 | 45 |
| Gene14302 | 227 | CG43088 | CG43088 | 3855 | 30.2 |
| Gene14726 | 228 | CG3848 | CG3848 | 3856 | 50 |

In a similar assay, the orthologue genes were tested in *Diabrotica barberi*. dsRNA molecules were diluted to the appropriate concentration such that 20 µl of solution was added to the surface of the diet in a 48-well plate, with a final overlay concentration of 1 µg dsRNA per well. One corn rootworm larvae was added to each well to have approximately 48 replicate larvae per dsRNA tested. Each 48-well plate was maintained at approximately 26° C. and 16:8 light:dark photoperiod. Mortality was recorded at different days after treatment. The results, shown in Table 3, demonstrate that dsRNA having complementarity to target genes, which are orthologues to *Sitophilus* target genes described in Table 1, are highly toxic to *Diabrotica barberi* (db; northern corn rootworm).

TABLE 3

Results of Db dsRNA primary screen

| Target ID | SEQ ID NO for Target | Putative Gene Name | Putative Flybase ID | SEQ ID NO: (RNA fragment) | Percent Mortality (Abbott corr.) |
|---|---|---|---|---|---|
| Gene00892 | 400 | Rop | CG15811 | 4028 | 87 |
| Gene01896 | 408 | arm | CG11579 | 4036 | 77 |
| Gene05129 | 416 | AP-1-2beta | CG12532 | 4044 | 88 |
| Gene06225 | 418 | CG1129 | CG1129 | 4046 | 67 |

TABLE 3-continued

Results of Db dsRNA primary screen

| Target ID | SEQ ID NO for Target | Putative Gene Name | Putative Flybase ID | SEQ ID NO: (RNA fragment) | Percent Mortality (Abbott corr.) |
|---|---|---|---|---|---|
| Gene08627 | 420 | mesh | CG31004 | 4048 | 84 |
| Gene08867 | 422 | alpha-Cat | CG17947 | 4050 | 96 |
| Gene11055 | 437 | ATPsyndelta | CG2968 | 4065 | 61 |
| Gene12327 | 441 | Sec61alpha | CG9539 | 4069 | 70 |
| Gene13224 | 445 | RpL7A | CG3314 | 4073 | 79 |

2.4. Testing of dsRNA Samples Against WCR in a Dose Response Curve.

This example describes testing dsRNAs of the invention for biological activity against *Diabrotica virgifera virgifera* (Dv; western corn rootworm).

The dsRNA molecules described above were tested for toxicity against WCR in laboratory bioassays in a 10-fold dilution series starting from 0.1 µg dsRNA/well. Bioassays were performed using an RNA-treated artificial diet method as described above. Synthesized dsRNA molecules were diluted to the appropriate concentration such that 20 µl of solution was added to the surface of the diet in half of the wells of a 48-well plate, with a final overlay concentration of 0.1 µg, 0.01 µg, 0.001 µg and 0.0001 µg per well. One or two WCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 6 and 7 d post-infestation. dsRNA designed to target GFP was used as a negative control and dsRNA designed to target an ubiquitin gene of WCR was used as a positive control.

The results confirm that the dsRNA molecules designed to target mRNA transcribable from Dv genes are highly toxic to Dv. See Table 4. After correction for the control mortality on the GFP dsRNA, the estimated $LT_{50}$ (time to obtain 50% mortality to pest insect population) and $LC_{50}$ (dsRNA concentration required to obtain 50% mortality in test insect population) were calculated by curve fitting analysis. The % mortality at day 7 is based on 0.1 µg dsRNA/well. The LT50 is based on using 0.1 µg dsRNA and is measured in days. The LC50 is measured in µg dsRNA/well.

Example 3. Expression of an RNAi Molecule Comprising Target dsRNA in Corn Plants This example describes introducing a construct that expresses an interfering RNA molecule into plant cells.

Vector Construction

Expression vectors designed to produce hairpin RNAs (hpRNA) consist of a cassette containing a promoter, a sense strand, an intron functioning as a loop sequence, an antisense strand, and terminator. A binary vector comprising an expression cassette comprising a DNA sequence designed to produce a hpRNA targeting a nucleotide fragment of a target gene described above is constructed. The binary vector also contains a second cassette between the left and right borders, designed to express phosphomannose isomerase (PMI) which confers unto the plant cell the ability to metabolize mannose (U.S. Pat. Nos. 5,767,378 and 5,994,629, which are incorporated by reference herein) as a selectable marker during plant transformation. The vectors also contain selectable markers for selection in bacteria.

*Agrobacterium* Mediated Transformation

Each resulting plasmid containing the hairpin cassette is transformed into *Agrobacterium tumefaciens* using standard molecular biology techniques known to those skilled in the art. The vectors described above are transformed into maize. *Agrobacterium* transformation of immature maize embryos is performed essentially as described in Negrotto et al., 2000, Plant Cell Reports 19: 798-803. For this example, all media constituents are essentially as described in Negrotto et al., supra. However, various media constituents known in the art may be substituted. Following transformation, selection, and regeneration, plants are tested for the presence of the pmi gene and the hairpin dsRNA interfering RNA molecule. Positive plants from the PCR assay are transferred to the greenhouse and tested for resistance to at least *Diabrotica virgifera* (Dv, western corn rootworm).

Transgenic Maize Dv Insecticidal Assay

F1 progeny of transgenic maize plants comprising the transgene a binary vector described above are germinated and allowed to grow. A PMI ELISA strip test (Romer Labs SeedChek® PMI (#7000052)) is used to identify plants positive for the transgene and null, non-transgenic segregating sister plants. Each plant is infested with 10 neonate western corn rootworms at its base. Seven days after infestation, the survival and size of the rootworms are evaluated.

TABLE 4

DRC results of dsRNA against Dv

| Target ID | SEQ ID NO for Target | Putative Gene Name | Putative Flybase ID | SEQ ID NO: (RNA fragment) | Percent Mortality (Abbott corr.) | LC50 (µg/well) | LT50 (days) |
|---|---|---|---|---|---|---|---|
| Gene00892 | 176 | Rop | CG15811 | 3804 | 97.7 | 0.0101 | 5.1 |
| Gene01896 | 184 | arm | CG11579 | 3812 | 95.7 | 0.0027 | 3.1 |
| Gene05129 | 193 | AP-1-2beta | CG12532 | 3821 | 90.3 | 0.0003 | 5.1 |
| Gene06225 | 195 | CG1129 | CG1129 | 3823 | 85.4 | 0.0040 | 4.4 |
| Gene08627 | 197 | mesh | CG31004 | 3825 | 100 | 0.0010 | 3.2 |
| Gene08867 | 199 | alpha-Cat | CG17947 | 3827 | 97.7 | 0.0004 | 3.2 |
| Gene11055 | 214 | ATPsyndelta | CG2968 | 3842 | 84.3 | 0.0036 | 4.3 |
| Gene12327 | 218 | Sec61alpha | CG9539 | 3846 | 75.6 | 0.0048 | 6.0 |
| Gene13224 | 222 | RpL7A | CG3314 | 3850 | 83.4 | 0.0034 | 6.0 |

Additionally, the corn roots from each of the plants are examined for feeding damage. This experiment is repeated at least eight times each for F1 progeny of transgenic maize plants comprising the transgene of the binary vector.

Results of the bioassays include the number of Dv larvae recovered 7 days after infestation. Recovered rootworm are graded by size (Dv size), as medium (m), medium/big (mb), big (b), or very big (vb). Roots of the corn plants are also analyzed for feeding damage. "Minor" root damage indicates roots appear strong and healthy. "Noticeable" root damage indicates the roots are slightly weaker compared to controls. "Significant" root damage indicates that the smaller roots are damaged or missing. "Severe" root damage indicates only the largest roots remain attached to the plant.

It is expected that results will confirm that the transgenic corn plants expressing dsRNAs that target Dv genes have less root damage compared to the non-transgenic, negative control sister plants. Therefore, transgenic plants comprising an interfering RNA molecule of the invention are expected to have enhanced resistance to an insect pest as compared to a non-transgenic control plant.

Transgenic Maize CRW Root Assay

Transgenic maize expressing the transgene from a binary vector described above are grown and brace roots or crown roots from the plant are removed. Root pieces are placed on a 2% agar plate and infested with 80 to 100 L1 Dv larvae. Following an incubation in the dark 26° C. for 24 to 48 hours, the L1 larvae are transferred to a 48-well Dv diet plate and incubated in the dark at 26° C. and scored daily for mortality of the Dv larvae, up to 7 days post-infestation. This experiment is performed on three different transgenic maize events, and on a non-transgenic control maize plant. The percent mortality is calculated.

It is expected that results of this test will confirm that the transgenic corn plants expressing dsRNAs that target one or more Dv genes have an insecticidal effect on Dv insect pests. It is expected that this will further show that a transgenic plant comprising an interfering RNA molecule of the invention has enhanced resistance to an insect pest as compared to a non-transgenic control plant.

Example 4. Interfering RNA Molecules with a Second Insecticidal Agent Bioassays

This example illustrates the toxicity of interfering RNA molecules of the invention in combination with a second insecticidal agent.

Double stranded RNA molecules are produced against the one or more of the Dv target genes identified above. Additionally, a second insecticidal agent, for example mCry3A or eCry3.1Ab, is prepared. Both the RNA and the second insecticidal agent are tested in combination for toxicity against Dv larvae in laboratory bioassays as described above.

Example 5. Producing Targeted dsRNA Molecules by Bacterial Expression

This example describes producing dsRNA molecules engineered against identified insect targets using a bacterial expression system.

Hairpin cassettes are engineered for selected insect target genes as described above. The hairpin cassette comprises a T7 promoter operably linked to an antisense sequence of the target, further linked at the 3' end to a nucleic acid sequence which is capable of forming a loop structure, further linked at the 3' end to the corresponding sense sequence of the target, operably linked at the 3' end to a T7 terminator sequence. The hairpin cassette is introduced into a bacterial expression vector, for example pGCP295, via appropriate restriction sites, for example BamHI and NotI. The vector is then introduced into an *Escherichia coli* strain, for example, HT115(DE3)GA01, via electroporation using standard methods, and transformants are selected using kanamycin selection.

The bacteria containing the targeted dsRNA expression vector plasmid are grown in defined medium to a specific optical density and induced by addition of IPTG for a specific time period following standard methods and routine optimization. After induction, the bacteria are harvested by centrifugation, and the produced dsRNA molecules are collected.

Example 6. Activity of Bacterially Produced dsRNA Molecules Against Dv Larvae

This example describes testing of a sub-set of the identified target dsRNAs of the invention for biological activity against Dv when applied as a spray. dsRNA molecules are bacterially produced as described above for testing as a spray application. A negative control GFP dsRNA molecule is also produced.

Bioassays are performed using an RNA-treated artificial diet method. Briefly, molten artificial diet, modified from the diet of Marrone et al. 1985 (J. Econ. Entomol. 78:290-293), is poured into each well of 48-well plates and allowed to solidify. Bacterially produced dsRNA molecules are diluted to appropriate concentration so that 20 μl of solution is added to the surface of the diet in half of the wells of a 48-well plate. One or two Dv larvae are added to each well to have between 24 and 48 replicate larvae per dsRNA tested. Each 48-well plate is maintained at approximately 26° C. and 16:8 light:dark photoperiod. Mortality is recorded at 7 days after treatment.

It is expected that spray-applied RNAi molecules of the invention are active against Dv.

Example 7. Identification of Potential RNAi Lethal Genes in Flea Beetle

This example describes the testing of dsRNA molecules against target genes in the flea beetles, *Phyllotreta armoraciae* (Pa) *Phyllotreta nemorum* (Pn), *Phyllotreta cruciferae* (Pu), *Phyllotreta striolata* (Ps), *Phyllotreta atra* (Pt) and/or *Psylliodes chrysocephala* (Pc), that are orthologues of the *Sitophilus oryzae* target genes described in Table 1.

7.1. RNA Sequencing and Transcriptome Generation of Flea Beetle Insects.

The flea beetle transcriptomes were generated in a similar way as described for *Sitophilus oryzae*. With BLAST most of the orthologuous genes of the *Sitophilus oryzae* targets described in Table 1 were identified in the flea beetles transcriptomes, including for Pa (SEQ ID NOs:452-564), Pn (SEQ ID NOs:565-679), Pu (SEQ ID NOs:680-789), Ps (SEQ ID NOs:790-905), Pt (SEQ ID NOs:906-1020) and Pc (SEQ ID NOs:1021-1133).

7.2. dsRNA Synthesis of the Candidate Target Genes in Flea Beetles.

The same 96 well library synthesis platform was used to produce dsRNA samples for testing against flea beetles. The negative control (dsRNA against a Green Fluorescent Protein—GFP) and the positive control (dsRNA against the species specific ubiquitin protein) were produced in the same manner.

7.3. Testing of dsRNA Samples Against Flea Beetles.

The dsRNA molecules described above were tested for toxicity against different flea beetles in laboratory bioassays. Bioassays were performed using an RNA-treated artificial diet method. Briefly, synthesized dsRNA molecules were diluted to the appropriate concentration in a sucrose solution. The solution containing the dsRNA was divided over three wells of a 96-well plate, the final dose being 1 μg/μl dsRNA in 5% sucrose per well. The plates were then sealed and six pinholes per well were made through the seals. Eight adults per well were added to a 6-well plate which is attached to the reversed sample plate by the use of tape, allowing the insects to feed on the droplets. On day 3 the dsRNA solution was replaced by a 15% sucrose solution to keep the insects until the end of the assay. Each assay was maintained at approximately 25° C. and 16:8 light:dark photoperiod. Mortality was recorded at different days post-infestation, with the final survival percentage calculated at 10 up to 17 days with Abbott correction. dsRNA designed to target green fluorescent protein (GFP) was used as a negative control. dsRNA designed to the specific ubiquitin protein were used as a positive control.

Results confirm that dsRNAs having complementarity to target genes in one or more flea beetle species (Pa, Pn, Pu, Ps, Pt and Pc), which are orthologues to *Sitophilus* target genes described in Table 1, are toxic to the one or more flea beetle species. See Table 5A and 5B.

TABLE 5A

Activity of dsRNA against Pa flea beetles

| Target ID | SEQ ID NO for Target | Putative Gene Name | Putative Flybase ID | SEQ ID NO: (RNA fragment) | Percent Mortality (Abbott corr.) |
|---|---|---|---|---|---|
| Gene00116 | 454 | Rpt4 | CG3455 | 4082 | 90.1 |
| Gene00132 | 457 | pnr | CG10278 | 4085 | 46.7 |
| Gene00140 | 459 | Prosbeta3 | CG11981 | 4087 | 33.3 |
| Gene00143 | 460 | Tm-SR | CG2848 | 4088 | 6.3 |
| Gene00161 | 461 | Bap60 | CG4303 | 4089 | 72.7 |
| Gene00180 | 462 | Pop2 | CG5684 | 4090 | 59.1 |
| Gene00187 | 464 | CCT4 | CG5525 | 4092 | 11.0 |
| Gene00191 | 466 | SkpA | CG16983 | 4094 | 23.8 |
| Gene00196 | 467 | mts | CG7109 | 4095 | 23.8 |
| Gene00220 | 469 | CCT7 | CG8351 | 4097 | 23.8 |
| Gene00228 | 470 | Dhc64C | CG7507 | 4098 | 31.8 |
| Gene00236 | 472 | pont | CG4003 | 4100 | 40.9 |
| Gene00237 | 473 | Cpsf100 | CG1957 | 4101 | 54.5 |
| Gene00242 | 475 | Rpn8 | CG3416 | 4103 | 95.2 |
| Gene00245 | 476 | CCT3 | CG8977 | 4104 | 36.4 |
| Gene00266 | 477 | Prosbeta6 | CG4097 | 4105 | 92.2 |
| Gene00269 | 479 | CCT5 | CG8439 | 4107 | 50.0 |
| Gene00276 | 480 | Roc1a | CG16982 | 4108 | 26.9 |
| Gene00277 | 481 | CCT2 | CG7033 | 4109 | 68.2 |
| Gene00281 | 482 | Prosalpha6 | CG4904 | 4110 | 68.4 |
| Gene00282 | 483 | fand | CG6197 | 4111 | 22.1 |
| Gene00284 | 485 | RpL8 | CG1263 | 4113 | 74.2 |
| Gene00289 | 487 | CCT6 | CG8231 | 4115 | 81.8 |
| Gene00323 | 492 | RpS8 | CG7808 | 4120 | 56.7 |
| Gene00325 | 493 | Rpn11 | CG18174 | 4121 | 100.0 |
| Gene00340 | 495 | Ykt6 | CG1515 | 4123 | 45.5 |
| Gene00343 | 496 | Prosalpha5 | CG10938 | 4124 | 55.5 |
| Gene00356 | 497 | Vha44 | CG8048 | 4125 | 64.5 |
| Gene00416 | 503 | Rpn6 | CG10149 | 4131 | 90.0 |
| Gene00424 | 505 | TER94 | CG2331 | 4133 | 72.7 |
| Gene00428 | 506 | cpb | CG17158 | 4134 | 76.0 |
| Gene00532 | 508 | RpL4 | CG5502 | 4136 | 56.3 |
| Gene00557 | 510 | ncm | CG12750 | 4138 | 30.1 |
| Gene00892 | 511 | Rop | CG15811 | 4139 | 34.7 |
| Gene01649 | 517 | Vha55 | CG17369 | 4145 | 23.8 |
| Gene03652 | 523 | AP-1sigma | CG5864 | 4151 | 81.8 |
| Gene05081 | 526 | pAbp | CG5119 | 4154 | 85.7 |
| Gene05129 | 527 | AP-1-2beta | CG12532 | 4155 | 13.8 |
| Gene05740 | 528 | RpL12 | CG3195 | 4156 | 81.1 |
| Gene06225 | 529 | CG1129 | CG1129 | 4157 | 8.7 |
| Gene08627 | 531 | mesh | CG31004 | 4159 | 73.3 |
| Gene08840 | 532 | RpLP2 | CG4918 | 4160 | 81.5 |
| Gene08867 | 533 | alpha-Cat | CG17947 | 4161 | 30.6 |
| Gene09268 | 535 | Sar1 | CG7073 | 4163 | 77.9 |
| Gene10001 | 539 | Rpn7 | CG5378 | 4167 | 60.9 |
| Gene11055 | 550 | ATPsyndelta | CG2968 | 4178 | 11.0 |
| Gene12327 | 554 | Sec61alpha | CG9539 | 4182 | 85.3 |

TABLE 5B

Activity of dsRNA against Pu flea beetles

| Target ID | SEQ ID NO for Target | Putative Gene Name | Putative Flybase ID | SEQ ID NO: (RNA fragment) | Percent Mortality (Abbott corr.) |
|---|---|---|---|---|---|
| Gene00111 | 681 | CstF64 | CG7697 | 4309 | 49.0 |
| Gene00116 | 682 | Rpt4 | CG3455 | 4310 | 96.3 |
| Gene00120 | 683 | Prosalpha3 | CG9327 | 4311 | 63.0 |
| Gene00129 | 684 | Rpn1 | CG7762 | 4312 | 63.0 |
| Gene00132 | 685 | pnr | CG10278 | 4313 | 88.9 |
| Gene00134 | 686 | garz | CG8487 | 4314 | 40.7 |
| Gene00140 | 687 | Prosbeta3 | CG11981 | 4315 | 100.0 |
| Gene00161 | 689 | Bap60 | CG4303 | 4317 | 74.8 |
| Gene00183 | 692 | CG7483 | CG7483 | 4320 | 42.6 |
| Gene00187 | 693 | CCT4 | CG5525 | 4321 | 40.7 |
| Gene00190 | 694 | Rpt3 | CG16916 | 4322 | 81.5 |
| Gene00196 | 696 | mts | CG7109 | 4324 | 77.8 |
| Gene00213 | 697 | Ubi-p63E | CG11624 | 4325 | 88.9 |
| Gene00220 | 698 | CCT7 | CG8351 | 4326 | 14.4 |
| Gene00233 | 699 | l(2)37Cb | CG10689 | 4327 | 37.0 |
| Gene00236 | 700 | pont | CG4003 | 4328 | 40.8 |
| Gene00237 | 701 | Cpsf100 | CG1957 | 4329 | 25.5 |
| Gene00238 | 702 | Sf3a1 | CG16941 | 4330 | 40.7 |
| Gene00242 | 703 | Rpn8 | CG3416 | 4331 | 100.0 |
| Gene00245 | 704 | CCT3 | CG8977 | 4332 | 81.5 |
| Gene00266 | 705 | Prosbeta6 | CG4097 | 4333 | 92.6 |
| Gene00269 | 707 | CCT5 | CG8439 | 4335 | 66.7 |
| Gene00276 | 708 | Roc1a | CG16982 | 4336 | 59.3 |
| Gene00277 | 709 | CCT2 | CG7033 | 4337 | 48.2 |
| Gene00281 | 710 | Prosalpha6 | CG4904 | 4338 | 81.5 |
| Gene00282 | 711 | fand | CG6197 | 4339 | 74.1 |
| Gene00284 | 713 | RpL8 | CG1263 | 4341 | 40.7 |
| Gene00286 | 714 | His3:CG31613 | CG31613 | 4342 | 10.4 |
| Gene00289 | 715 | CCT6 | CG8231 | 4343 | 59.3 |
| Gene00305 | 716 | Uba1 | CG1782 | 4344 | 37.0 |
| Gene00306 | 717 | Hel25E | CG7269 | 4345 | 61.8 |
| Gene00313 | 719 | Slu7 | CG1420 | 4347 | 51.9 |
| Gene00323 | 720 | RpS8 | CG7808 | 4348 | 100.0 |
| Gene00325 | 721 | Rpn11 | CG18174 | 4349 | 100.0 |
| Gene00337 | 722 | Rpt6 | CG1489 | 4350 | 74.1 |
| Gene00340 | 723 | Ykt6 | CG1515 | 4351 | 88.9 |
| Gene00343 | 724 | Prosalpha5 | CG10938 | 4352 | 100.0 |
| Gene00367 | 726 | CCT1 | CG5374 | 4354 | 33.3 |
| Gene00368 | 727 | Prosbeta7 | CG12000 | 4355 | 63.0 |
| Gene00379 | 729 | pea | CG8241 | 4357 | 11.1 |
| Gene00384 | 730 | CG9175 | CG9175 | 4358 | 60.6 |
| Gene00416 | 731 | Rpn6 | CG10149 | 4359 | 92.6 |
| Gene00418 | 732 | Lam | CG6944 | 4360 | 9.0 |
| Gene00424 | 733 | TER94 | CG2331 | 4361 | 100.0 |
| Gene00428 | 734 | cpb | CG17158 | 4362 | 93.3 |
| Gene00532 | 736 | RpL4 | CG5502 | 4364 | 85.2 |
| Gene00544 | 737 | Spt6 | CG12225 | 4365 | 44.4 |
| Gene00557 | 738 | ncm | CG12750 | 4366 | 96.3 |

TABLE 5B-continued

Activity of dsRNA against Pu flea beetles

| Target ID | SEQ ID NO for Target | Putative Gene Name | Putative Flybase ID | SEQ ID NO: (RNA fragment) | Percent Mortality (Abbott corr.) |
|---|---|---|---|---|---|
| Gene00892 | 739 | Rop | CG15811 | 4367 | 70.4 |
| Gene00949 | 740 | Sec10 | CG6159 | 4368 | 12.3 |
| Gene01074 | 741 | Sf3a2 | CG10754 | 4369 | 55.6 |
| Gene01187 | 742 | SmD3 | CG8427 | 4370 | 23.0 |
| Gene01510 | 743 | UQCR-C2 | CG4169 | 4371 | 41.5 |
| Gene01576 | 744 | Bet1 | CG14084 | 4372 | 100.0 |
| Gene01649 | 745 | Vha55 | CG17369 | 4373 | 48.1 |
| Gene01896 | 746 | arm | CG11579 | 4374 | 96.3 |
| Gene02220 | 747 | CG9667 | CG9667 | 4375 | 25.9 |
| Gene02775 | 748 | Cdc5 | CG6905 | 4376 | 60.2 |
| Gene03652 | 749 | AP-1sigma | CG5864 | 4377 | 100.0 |
| Gene05081 | 752 | pAbp | CG5119 | 4380 | 85.2 |
| Gene05129 | 753 | AP-1-2beta | CG12532 | 4381 | 96.3 |
| Gene05740 | 754 | RpL12 | CG3195 | 4382 | 64.6 |
| Gene06225 | 755 | CG1129 | CG1129 | 4383 | 51.8 |
| Gene06978 | 756 | cpa | CG10540 | 4384 | 100.0 |
| Gene08627 | 757 | mesh | CG31004 | 4385 | 92.6 |
| Gene08840 | 758 | RpLP2 | CG4918 | 4386 | 18.5 |
| Gene08867 | 759 | alpha-Cat | CG17947 | 4387 | 70.4 |
| Gene08949 | 760 | Nup62 | CG6251 | 4388 | 33.3 |
| Gene09268 | 761 | Sar1 | CG7073 | 4389 | 96.3 |
| Gene09812 | 763 | Sac1 | CG9128 | 4391 | 21.5 |
| Gene09966 | 764 | atms | CG2503 | 4392 | 18.5 |
| Gene10001 | 765 | Rpn7 | CG5378 | 4393 | 92.6 |
| Gene10142 | 767 | DNApol-alpha180 | CG6349 | 4395 | 45.5 |
| Gene10189 | 768 | rept | CG9750 | 4396 | 22.2 |
| Gene10649 | 770 | Rho1 | CG8416 | 4398 | 27.0 |
| Gene10683 | 771 | Nup154 | CG4579 | 4399 | 22.2 |
| Gene10692 | 772 | Nup160 | CG4738 | 4400 | 38.3 |
| Gene10724 | 773 | Cse1 | CG13281 | 4401 | 22.8 |
| Gene11055 | 776 | ATPsyndelta | CG2968 | 4404 | 44.4 |
| Gene11554 | 777 | nudC | CG9710 | 4405 | 48.1 |
| Gene11636 | 778 | Srp19 | CG4457 | 4406 | 70.4 |
| Gene11792 | 779 | cm | CG3193 | 4407 | 85.2 |
| Gene12327 | 780 | Sec61alpha | CG9539 | 4408 | 92.6 |
| Gene12739 | 781 | Cyt-c1 | CG4769 | 4409 | 44.4 |
| Gene12888 | 782 | CG6015 | CG6015 | 4410 | 37.0 |
| Gene13224 | 783 | RpL7A | CG3314 | 4411 | 59.3 |
| Gene13823 | 784 | betaggt-II | CG18627 | 4412 | 70.4 |
| Gene13837 | 785 | Fs(2)Ket | CG2637 | 4413 | 30.0 |
| Gene13977 | 786 | noi | CG2925 | 4414 | 42.4 |

Example 8. Identification of RNAi Lethal Genes in the Pollen Beetle, *Meligethes aeneus*

This example describes the testing of dsRNA molecules against one or more target genes in *Meligethes aeneus* (Ma, pollen beetle) (SEQ ID NOs:1134-1248), that are orthologues of the *Sitophilus oryzae* target genes described in Table 1.

8.1. dsRNA Synthesis of Candidate Target Genes in Pollen Beetle.

The same 96 well library synthesis platform described above was used to produce dsRNA samples for testing against Ma pollen beetle. Templates for the dsRNA molecules were produced based on publicly available transcriptome information for the Ma targets. A negative control (dsRNA against a Green Fluorescent Protein—GFP) and a positive control (dsRNA against the species specific ubiquitin protein) were produced in the same manner.

8.2. Testing of dsRNA Molecules Against Pollen Beetle.

The dsRNA molecules described above were tested for toxicity against Ma pollen beetle in laboratory bioassays. Bioassays were performed using an RNA-treated artificial diet method, in a similar way as described above for the flea beetle. Briefly, synthesized dsRNA molecules were diluted to the appropriate concentration in a sucrose solution. The solution containing the dsRNA was divided over three wells of a 96-well plate, the final dose being 1 μg/μl dsRNA in 5% sucrose per well. The plates were then sealed and six pinholes per well are made through the seals. Eight adults per well were added to a 6-well plate which was attached to the reversed sample plate by the use of tape, allowing the insects to feed on the droplets. On day 3 the dsRNA solution was replaced by a 15% sucrose solution to keep the insects until the end of the assay. Each assay was maintained at approximately 25° C. and 16:8 light:dark photoperiod. Mortality was recorded at different days post-infestation, with the final survival percentage calculated at 8 or 10 days with Abbott's correction. dsRNA designed to target green fluorescent protein (GFP) was used as a negative control. dsRNA designed to the specific ubiquitin protein was used as a positive control.

Results confirm that dsRNAs having complementarity to target genes in Ma pollen beetles, which are orthologues to *Sitophilus* target genes described in Table 1, are toxic to the Ma pollen beetle.

TABLE 6

Activity of dsRNA against pollen beetle

| Target ID | SEQ ID NO for Target | Putative gene name | Putative Flybase ID | SEQ ID NO: (RNA fragment) | Percent Mortality (Abbott corr.) |
|---|---|---|---|---|---|
| Gene00111 | 1135 | CstF64 | CG7697 | 4763 | 40 |
| Gene00116 | 1136 | Rpt4 | CG3455 | 4764 | 27 |
| Gene00120 | 1137 | Prosalpha3 | CG9327 | 4765 | 50 |
| Gene00129 | 1138 | Rpn1 | CG7762 | 4766 | 30 |
| Gene00132 | 1139 | GATAe | CG10278 | 4767 | 10 |
| Gene00134 | 1140 | garz | CG8487 | 4768 | 7 |
| Gene00140 | 1141 | Prosbeta3 | CG11981 | 4769 | 82 |
| Gene00161 | 1143 | Bap60 | CG4303 | 4771 | 33 |
| Gene00180 | 1145 | Pop2 | CG5684 | 4773 | 37 |
| Gene00183 | 1146 | CG7483 | CG7483 | 4774 | 48 |
| Gene00187 | 1147 | CCT4 | CG5525 | 4775 | 60 |
| Gene00190 | 1148 | Rpt3 | CG16916 | 4776 | 76 |
| Gene00196 | 1150 | mts | CG7109 | 4778 | 55 |
| Gene00213 | 1151 | Ubi-p63E | CG11624 | 4779 | 100 |
| Gene00220 | 1152 | CCT7 | CG8351 | 4780 | 70 |
| Gene00228 | 1153 | Dhc64C | CG7507 | 4781 | 56 |
| Gene00233 | 1154 | l(2)37Cb | CG10689 | 4782 | 59 |
| Gene00236 | 1155 | pont | CG4003 | 4783 | 20 |
| Gene00237 | 1156 | Cpsf100 | CG1957 | 4784 | 67 |
| Gene00238 | 1157 | Sf3a1 | CG16941 | 4785 | 54 |
| Gene00242 | 1158 | Rpn8 | CG3416 | 4786 | 73 |
| Gene00245 | 1159 | CCT3 | CG8977 | 4787 | 81 |
| Gene00266 | 1160 | Prosbeta6 | CG4097 | 4788 | 35 |
| Gene00269 | 1162 | CCT5 | CG8439 | 4790 | 73 |
| Gene00276 | 1163 | Roc1a | CG16982 | 4791 | 58 |
| Gene00277 | 1164 | CCT2 | CG7033 | 4792 | 65 |
| Gene00281 | 1165 | Prosalpha6 | CG4904 | 4793 | 83 |
| Gene00282 | 1166 | fand | CG6197 | 4794 | 70 |
| Gene00284 | 1168 | RpL8 | CG1263 | 4796 | 30 |
| Gene00286 | 1169 | His3:CG31613 | CG31613 | 4797 | 20 |
| Gene00289 | 1170 | CCT6 | CG8231 | 4798 | 63 |
| Gene00305 | 1171 | Uba1 | CG1782 | 4799 | 100 |
| Gene00306 | 1172 | Hel25E | CG7269 | 4800 | 87 |
| Gene00309 | 1173 | Rpn3 | CG42641 | 4801 | 93 |
| Gene00313 | 1174 | Slu7 | CG1420 | 4802 | 83 |
| Gene00323 | 1175 | RpS8 | CG7808 | 4803 | 80 |
| Gene00325 | 1176 | Rpn11 | CG18174 | 4804 | 90 |
| Gene00337 | 1177 | Rpt6 | CG1489 | 4805 | 90 |
| Gene00340 | 1178 | Ykt6 | CG1515 | 4806 | 93 |
| Gene00343 | 1179 | Prosalpha5 | CG10938 | 4807 | 81 |
| Gene00356 | 1180 | Vha44 | CG8048 | 4808 | 80 |
| Gene00367 | 1181 | CCT1 | CG5374 | 4809 | 83 |

TABLE 6-continued

Activity of dsRNA against pollen beetle

| Target ID | SEQ ID NO for Target | Putative gene name | Putative Flybase ID | SEQ ID NO: (RNA fragment) | Percent Mortality (Abbott corr.) |
|---|---|---|---|---|---|
| Gene00368 | 1182 | Prosbeta7 | CG12000 | 4810 | 76 |
| Gene00384 | 1185 | CG9175 | CG9175 | 4813 | 90 |
| Gene00416 | 1186 | Rpn6 | CG10149 | 4814 | 97 |
| Gene00424 | 1188 | TER94 | CG2331 | 4816 | 93 |
| Gene00428 | 1189 | cpb | CG17158 | 4817 | 3 |
| Gene00532 | 1191 | RpL4 | CG5502 | 4819 | 87 |
| Gene00544 | 1192 | Spt6 | CG12225 | 4820 | 100 |
| Gene00892 | 1194 | Rop | CG15811 | 4822 | 78 |
| Gene00949 | 1195 | Sec10 | CG6159 | 4823 | 25 |
| Gene01074 | 1196 | Sf3a2 | CG10754 | 4824 | 20 |
| Gene01510 | 1198 | UQCR-C2 | CG4169 | 4826 | 100 |
| Gene01576 | 1199 | Bet1 | CG14084 | 4827 | 100 |
| Gene01649 | 1200 | Vha55 | CG17369 | 4828 | 95 |
| Gene01896 | 1202 | arm | CG11579 | 4830 | 91 |
| Gene02220 | 1203 | CG9667 | CG9667 | 4831 | 86 |
| Gene02775 | 1206 | Cdc5 | CG6905 | 4834 | 100 |
| Gene03652 | 1207 | AP-1sigma | CG5864 | 4835 | 100 |
| Gene03841 | 1208 | CG11779 | CG11779 | 4836 | 91 |
| Gene05129 | 1212 | AP-1-2beta | CG12532 | 4840 | 88 |
| Gene05740 | 1213 | RpL12 | CG3195 | 4841 | 100 |
| Gene06225 | 1214 | CG1129 | CG1129 | 4842 | 86 |
| Gene06978 | 1215 | cpa | CG10540 | 4843 | 67 |
| Gene08627 | 1216 | mesh | CG31004 | 4844 | 100 |
| Gene08867 | 1217 | alpha-Cat | CG17947 | 4845 | 88 |
| Gene08949 | 1218 | Nup62 | CG6251 | 4846 | 92 |
| Gene09268 | 1219 | Sar1 | CG7073 | 4847 | 100 |
| Gene09812 | 1221 | Sac1 | CG9128 | 4849 | 57 |
| Gene09966 | 1222 | atms | CG2503 | 4850 | 61 |
| Gene10001 | 1223 | Rpn7 | CG5378 | 4851 | 100 |
| Gene10142 | 1225 | DNApol-alpha180 | CG6349 | 4853 | 19 |
| Gene10189 | 1226 | rept | CG9750 | 4854 | 61 |
| Gene10649 | 1228 | Rho1 | CG8416 | 4856 | 81 |
| Gene10692 | 1230 | Nup160 | CG4738 | 4858 | 73 |
| Gene10724 | 1231 | Cse1 | CG13281 | 4859 | 85 |
| Gene10755 | 1232 | asf1 | CG9383 | 4860 | 11 |
| Gene11055 | 1234 | ATPsyndelta | CG2968 | 4862 | 65 |
| Gene11554 | 1235 | nudC | CG9710 | 4863 | 61 |
| Gene11636 | 1236 | Srp19 | CG4457 | 4864 | 100 |
| Gene11792 | 1237 | cm | CG3193 | 4865 | 100 |
| Gene12327 | 1238 | Sec61alpha | CG9539 | 4866 | 10 |
| Gene12739 | 1240 | Cyt-c1 | CG4769 | 4868 | 65 |
| Gene12888 | 1241 | CG6015 | CG6015 | 4869 | 53 |
| Gene13224 | 1242 | RpL7A | CG3314 | 4870 | 88 |
| Gene13823 | 1243 | betaggt-II | CG18627 | 4871 | 77 |
| Gene13837 | 1244 | Fs(2)Ket | CG2637 | 4872 | 23 |
| Gene13977 | 1245 | noi | CG2925 | 4873 | 81 |
| Gene14143 | 1246 | SmB | CG5352 | 4874 | 83 |

Example 9. Identification of Potential RNAi Lethal Genes in *Ceutorhynchus* Spp

This example describes the testing of dsRNA molecules against target genes in *Ceutorhynchus assimilis* (Ca, cabbage seedpod weevil), that are orthologues of the *Sitophilus oryzae* target genes described in Table 1.

9.1. RNA Sequencing and Transcriptome Generation of *Ceutorhynchus* Spp.

The *Ceutorhynchus* transcriptomes were generated in a similar way as described for *Sitophilus oryzae*. With BLAST most of the orthologuous genes of the *Sitophilus oryzae* targets described in Table 1 were identified in the *Ceutorhynchus* transcriptomes, represented herein as SEQ ID NOs:1249-1360.

9.2. dsRNA Synthesis of the Candidate Target Genes in *Ceutorhynchus assimilis*.

The same 96 well library synthesis platform as described above is used to produce dsRNA samples for testing against *Ceutorhynchus assimilis*. A negative control (dsRNA against a Green Fluorescent Protein—GFP) and a positive control (dsRNA against the species specific ubiquitin protein) are produced in the same manner.

9.3. Testing of dsRNA Samples Against *Ceutorhynchus assimilis*.

The dsRNA molecules described above are tested for toxicity against *Ceutorhynchus assimilis* (Ca; cabbage seedpod weevil) in laboratory bioassays. Bioassays are performed using an RNA-treated artificial diet method, in a similar way as described above for the flea beetles. Briefly, synthesized dsRNA molecules are diluted to the appropriate concentration in a sucrose solution. The solution containing the dsRNA is divided over three wells of a 96-well plate, the final dose being 1 μg/μl dsRNA in 5% sucrose per well. The plates are then sealed and six pinholes per well are made through the seals. Eight adults per well are added to a 6-well plate which is attached to the reversed sample plate by the use of tape, allowing the insects to feed on the droplets. On day 3 the dsRNA solution is replaced by a 15% sucrose solution to keep the insects until the end of the assay. Each assay is maintained at approximately 25° C. and 16:8 light:dark photoperiod. Mortality is recorded at different days post-infestation, with the final survival percentage calculated at 8 or 10 days with Abbott correction. dsRNA designed to target green fluorescent protein (GFP) is used as a negative control. dsRNA designed to the specific ubiquitin protein is used as a positive control.

It is expected that dsRNAs having complementarity to one or more target genes in a Ca beetle (e.g., comprising any one of SEQ ID NOs:4877-4988), which are orthologues to *Sitophilus* target genes described in Table 1, are toxic to the Ca beetle.

Example 10. Activity of dsRNA Molecules in a Spray Application Assay Against Canola Pests This example describes testing of a sub-set of the identified target dsRNAs of the invention for biological activity against insect pests of oil seed rape when applied as a spray. dsRNA molecules are bacterially produced as described above for testing as a spray application on planta. A negative control GFP dsRNA molecule is also produced.

Three 2-3 week old oil seed rape plants (*Brassica napus* L.) are sprayed with bacterially produced dsRNA (200 μg per 3 plants), dissolved in a sucrose solution. 15 insects are put on the plant after spraying, and the infested plant is maintained in a container closed with a mesh. Three days after the initial spraying, the plant is replaced by a second plant sprayed with the same bacterial lysate sucrose solution. Six days after the initial spraying the insects are transferred to a petri dish containing only a sucrose solution (15% sucrose).

Example 11. Expression of an RNAi Molecule Comprising Target dsRNA in Canola Plants This example describes introducing a construct that expresses an interfering RNA molecule into canola plant cells.

11.1. Vector Construction

Expression vectors designed to produce hairpin RNAs (hpRNA) consist of a cassette containing a promoter, a sense strand, an intron functioning as a loop sequence, an antisense strand, and terminator. The hpRNA targets at least 21 nucleotides of an endogenous gene target as described above. The hpRNA expression cassette is cloned into a binary vector. The binary vector also contains a second expression cassette between the left and right T-DNA borders which is designed to express a selectable marker for selection of transgenic cells, tissues, and/or plants following plant transformation. The binary vector also contains selectable markers for selection of the presence of the binary vector bacteria.

11.2. *Agrobacterium*-Mediated Transformation of *Brassica napus*

Each resulting plasmid containing the hairpin cassette is transformed into *Agrobacterium tumefaciens* using standard molecular biology techniques known to those skilled in the art. The vectors described above are transformed into canola.

Stably transformed *Brassica napus* cv. 'Westar' events are obtained using an adapted published floral dip protocol (Wang et al. 2003). Adult flowering plants are infiltrated twice under vacuum with an *Agrobacterium tumefaciens* suspension. The strain used is C58C1RifR harboring the pGV3101 Ti plasmid and a binary vector containing two plant expression cassettes, one for the insect target derived dsRNA which is inserted as a hairpin and an nptII based plant selectable marker.

After the two infiltrations, performed a week apart, the plants are allowed to mature and set seed. To identify the transformation events, the seed is soaked for 2 days in 300 mg/l kanamycin sulphate solution and then sown out into soil (Li et al. 2010). One week after sowing, the putative positive seedlings are identified due to their healthy green expanded cotyledons versus the smaller, shrunken bleached non-transformed seedlings.

The transgenic status of the putative events is checked by plus/minus PCR for the presence of the nptII sequence. Positive events are grown up to flowering at which point racemes are removed for insect bioassay.

For the insect feeding bioassay, racemes are removed from the plant when in bud and immediately the cut end is put through the plastic lid of a 20 ml glass vial containing water. Each raceme is infested with 10-15 wild caught *M. aeneus* adults, and mortality is scored up till day 14 post infestation. The racemes are changed for fresh at day 7.

The events described above are tested for toxicity against flea beetles and/or *Ceuthorrhynchus* spp., in laboratory bioassays. For the insect feeding bioassay three 2-3 week old oil seed rape plants (*Brassica napus*) are infested with 10-12 insects and kept in a container closed with a mesh. Six days after setup the insects are transferred to a wild-type plant. The number of dead adults is recorded every two to three days.

Example 12. Identification of Potential RNAi Lethal Genes in Soy Stink Bugs

This example describes the testing of dsRNA molecules against target genes in one or more soybean stink bug species, *Nezara viridula* (Nv), *Euschistus heros* (Eh) and/or *Piezodorus guildinii* (Pg), that are orthologues of the *Sitophilus oryzae* target genes described in Table 1.

12.1. RNA Sequencing and Transcriptome Generation of Soybean Stink Bugs.

The transcriptomes of soybean stink bugs were generated in a similar way as described for *Sitophilus oryzae* above. With BLAST most of the orthologuous genes of the *Sitophilus oryzae* targets described in Table 1 were identified in the three different soy stink bug transcriptomes; for Nv (SEQ ID NOs:1361-1473), Eh (SEQ ID NOs:1474-1586) and Pg (SEQ ID NOs:1587-1699).

12.2. dsRNA Synthesis of the Candidate Target Genes in Soy Stink Bugs.

The same 96 well library synthesis platform was used to produce dsRNA samples for testing against Nv soy stink bugs. The negative control (dsRNA against a Green Fluorescent Protein—GFP) and the positive control (dsRNA against the species specific ubiquitin protein) were produced in the same manner. The same platform is used for Eh and Pg stink bugs.

12.3. Testing of dsRNA Samples Against Soy Stink Bugs

In vitro assays on Nv stink bug nymphs were performed in 96-well nylon mesh filter plates. Each well of a 96-well filter plate housed a second instar nymph exposed to a parafilm sachet containing a mixture of 15% sucrose and 1 μg/μl dsRNA. Plates were stored in plastic boxes in a rearing chamber at 26° C., 65% RH, and 16:8 hours light:dark. Survival was recorded from 3 to 10 days post exposure to dsRNA. dsRNA molecules to the different targets described above were tested. dsRNA of non target GFP was used as a negative control. A positive control dsRNA target known to be lethal was also included in the assays. The same testing is performed on Eh and Pg stink bugs.

Table 7 shows the results for dsRNAs having complementarity to one or more target genes in the soybean stinkbug Nv, which are orthologues to *Sitophilus* target genes described in Table 1, are toxic to an Nv stinkbug. It is expected that dsRNAs having complementarity to one or more target genes in the soybean stinkbugs Eh and/or Pg, which are orthologues to *Sitophilus* target genes described in Table 1, are toxic to a Eh stinkbug and/or a Pg stinkbug.

TABLE 7

Activity of dsRNA against *Nezara viridula*

| Target ID | SEQ ID NO for Target | Putative gene name | Putative Flybase ID | SEQ ID NO: (RNA fragment) | Percent Mortality (Abbott corr.) |
|---|---|---|---|---|---|
| Gene00101 | 1361 | cactin | CG1676 | 4989 | 36 |
| Gene00111 | 1362 | CstF64 | CG7697 | 4990 | 7 |
| Gene00116 | 1363 | Rpt4 | CG3455 | 4991 | 59 |
| Gene00120 | 1364 | Prosalpha3 | CG9327 | 4992 | 82 |
| Gene00129 | 1365 | Rpn1 | CG7762 | 4993 | 45 |
| Gene00132 | 1366 | pnr | CG10278 | 4994 | 0 |
| Gene00134 | 1367 | garz | CG8487 | 4995 | 45 |
| Gene00140 | 1368 | Prosbeta3 | CG11981 | 4996 | 66 |
| Gene00143 | 1369 | Trn-SR | CG2848 | 4997 | 18 |
| Gene00161 | 1370 | Bap60 | CG4303 | 4998 | 41 |
| Gene00171 | 1371 | l(1)10Bb | CG1639 | 4999 | 3 |
| Gene00180 | 1372 | Pop2 | CG5684 | 5000 | 13 |
| Gene00183 | 1373 | CG7483 | CG7483 | 5001 | 39 |
| Gene00187 | 1374 | CCT4 | CG5525 | 5002 | 68 |
| Gene00190 | 1375 | Rpt3 | CG16916 | 5003 | 62 |
| Gene00191 | 1376 | SkpA | CG16983 | 5004 | 8 |
| Gene00196 | 1377 | mts | CG7109 | 5005 | 68 |
| Gene00213 | 1378 | Ubi-p63E | CG11624 | 5006 | 63 |
| Gene00228 | 1380 | Dhc64C | CG7507 | 5008 | 74 |
| Gene00233 | 1381 | l(2)37Cb | CG10689 | 5009 | 1 |
| Gene00236 | 1382 | pont | CG4003 | 5010 | 56 |
| Gene00237 | 1383 | Cpsf100 | CG1957 | 5011 | 0 |
| Gene00238 | 1384 | Sf3a1 | CG16941 | 5012 | 38 |
| Gene00242 | 1385 | Rpn8 | CG3416 | 5013 | 21 |
| Gene00245 | 1386 | CCT3 | CG8977 | 5014 | 68 |
| Gene00266 | 1387 | Prosbeta6 | CG4097 | 5015 | 93 |
| Gene00268 | 1388 | Ufd1-like | CG6233 | 5016 | 32 |
| Gene00269 | 1389 | CCT5 | CG8439 | 5017 | 89 |

TABLE 7-continued

Activity of dsRNA against Nezara viridula

| Target ID | SEQ ID NO for Target | Putative gene name | Putative Flybase ID | SEQ ID NO: (RNA fragment) | Percent Mortality (Abbott corr.) |
|---|---|---|---|---|---|
| Gene00276 | 1390 | Roc1a | CG16982 | 5018 | 0 |
| Gene00277 | 1391 | CCT2 | CG7033 | 5019 | 76 |
| Gene00281 | 1392 | Prosalpha6 | CG4904 | 5020 | 65 |
| Gene00282 | 1393 | fand | CG6197 | 5021 | 51 |
| Gene00283 | 1394 | Spx | CG3780 | 5022 | 0 |
| Gene00284 | 1395 | RpL8 | CG1263 | 5023 | 39 |
| Gene00286 | 1396 | His3:CG31613 | CG31613 | 5024 | 62 |
| Gene00289 | 1397 | CCT6 | CG8231 | 5025 | 84 |
| Gene00305 | 1398 | Uba1 | CG1782 | 5026 | 51 |
| Gene00309 | 1400 | Rpn3 | CG42641 | 5028 | 68 |
| Gene00313 | 1401 | Slu7 | CG1420 | 5029 | 23 |
| Gene00323 | 1402 | RpS8 | CG7808 | 5030 | 76 |
| Gene00325 | 1403 | Rpn11 | CG18174 | 5031 | 41 |
| Gene00337 | 1404 | Rpt6 | CG1489 | 5032 | 65 |
| Gene00340 | 1405 | Ykt6 | CG1515 | 5033 | 0 |
| Gene00343 | 1406 | Prosalpha5 | CG10938 | 5034 | 44 |
| Gene00356 | 1407 | Vha44 | CG8048 | 5035 | 37 |
| Gene00368 | 1409 | Prosbeta7 | CG12000 | 5037 | 71 |
| Gene00370 | 1410 | Exo84 | CG6095 | 5038 | 0 |
| Gene00379 | 1411 | pea | CG8241 | 5039 | 47 |
| Gene00384 | 1412 | CG9175 | CG9175 | 5040 | 31 |
| Gene00418 | 1414 | Lam | CG6944 | 5042 | 2 |
| Gene00428 | 1416 | cpb | CG17158 | 5044 | 38 |
| Gene00429 | 1417 | fs(1)h | CG2252 | 5045 | 0 |
| Gene00532 | 1418 | RpL4 | CG5502 | 5046 | 25 |
| Gene00544 | 1419 | Spt6 | CG12225 | 5047 | 12 |
| Gene00892 | 1421 | Rop | CG15811 | 5049 | 54 |
| Gene00949 | 1422 | Sec10 | CG6159 | 5050 | 1 |
| Gene01074 | 1423 | Sf3a2 | CG10754 | 5051 | 47 |
| Gene01187 | 1424 | SmD3 | CG8427 | 5052 | 42 |
| Gene01510 | 1425 | UQCR-C2 | CG4169 | 5053 | 60 |
| Gene01649 | 1427 | Vha55 | CG17369 | 5055 | 0 |
| Gene01896 | 1428 | arm | CG11579 | 5056 | 0 |
| Gene02220 | 1429 | CG9667 | CG9667 | 5057 | 40 |
| Gene02411 | 1430 | Ran | CG1404 | 5058 | 47 |
| Gene02760 | 1431 | Ssk | CG6981 | 5059 | 1 |
| Gene02775 | 1432 | Cdc5 | CG6905 | 5060 | 33 |
| Gene03652 | 1433 | AP-1sigma | CG5864 | 5061 | 28 |
| Gene03841 | 1434 | CG11779 | CG11779 | 5062 | 0 |
| Gene04283 | 1435 | CG1542 | CG1542 | 5063 | 0 |
| Gene05081 | 1437 | pAbp | CG5119 | 5065 | 57 |
| Gene05129 | 1438 | AP-1-2beta | CG12532 | 5066 | 27 |
| Gene05740 | 1439 | RpL12 | CG3195 | 5067 | 13 |
| Gene06225 | 1440 | CG1129 | CG1129 | 5068 | 25 |
| Gene06978 | 1441 | cpa | CG10540 | 5069 | 27 |
| Gene08627 | 1442 | mesh | CG31004 | 5070 | 20 |
| Gene08840 | 1443 | RpLP2 | CG4918 | 5071 | 9 |
| Gene08867 | 1444 | alpha-Cat | CG17947 | 5072 | 63 |
| Gene08949 | 1445 | Nup62 | CG6251 | 5073 | 0 |
| Gene09268 | 1446 | Sar1 | CG7073 | 5074 | 40 |
| Gene09812 | 1447 | Sac1 | CG9128 | 5075 | 0 |
| Gene09966 | 1448 | atms | CG2503 | 5076 | 65 |
| Gene10001 | 1449 | Rpn7 | CG5378 | 5077 | 85 |
| Gene10086 | 1450 | Lpt | CG5591 | 5078 | 0 |
| Gene10142 | 1451 | DNApol-alpha180 | CG6349 | 5079 | 17 |
| Gene10189 | 1452 | rept | CG9750 | 5080 | 0 |
| Gene10549 | 1453 | Snr1 | CG1064 | 5081 | 23 |
| Gene10649 | 1454 | Rho1 | CG8416 | 5082 | 55 |
| Gene10683 | 1455 | Nup154 | CG4579 | 5083 | 0 |
| Gene10692 | 1456 | Nup160 | CG4738 | 5084 | 0 |
| Gene10724 | 1457 | Cse1 | CG13281 | 5085 | 64 |
| Gene10755 | 1458 | asf1 | CG9383 | 5086 | 0 |
| Gene11048 | 1459 | Tbp | CG9874 | 5087 | 18 |
| Gene11055 | 1460 | ATPsyndelta | CG2968 | 5088 | 47 |
| Gene11554 | 1461 | nudC | CG9710 | 5089 | 28 |
| Gene11636 | 1462 | Srp19 | CG4457 | 5090 | 0 |
| Gene12327 | 1464 | Sec61alpha | CG9539 | 5092 | 50 |
| Gene12548 | 1465 | Cbp20 | CG12357 | 5093 | 3 |
| Gene12739 | 1466 | Cyt-c1 | CG4769 | 5094 | 23 |
| Gene12888 | 1467 | CG6015 | CG6015 | 5095 | 18 |
| Gene13224 | 1468 | RpL7A | CG3314 | 5096 | 29 |
| Gene13823 | 1469 | betaggt-II | CG18627 | 5097 | 0 |
| Gene13837 | 1470 | Fs(2)Ket | CG2637 | 5098 | 59 |
| Gene13977 | 1471 | noi | CG2925 | 5099 | 45 |
| Gene14143 | 1472 | SmB | CG5352 | 5100 | 63 |
| Gene14302 | 1473 | CG43088 | CG43088 | 5101 | 0 |

Example 13. Activity of dsRNA Molecules in a Spray Application Assay

This example describes testing of a sub-set of the identified target dsRNAs of the invention for biological activity against stink bugs when applied as a spray. The production of bacterial lysate is described above.

Three 3 week old soy bean plants (Glycine max (L.) Jack) are sprayed with a about 15% sucrose solution containing bacterial lysate expressing non-targeting GFP dsRNA and target dsRNA molecules from the expression vectors described above. 25 second instar stink bug nymphs were then placed on each sprayed plant. Plants are placed in a box coated with fluon PTFE to prevent stink bug escape and stored in a rearing chamber (26° C., 65% RH, with 16:8 hours l:d). Photographs are taken on a daily basis to record plant health. The nymph survival rate is recorded 3 to 14 days post exposure to the sprayed plant. These experiments are performed using either E. heros, N. viridula, or P. guildinii nymphs. A dsRNA of non-target GFP is used as a negative control and a dsRNA designed against a known a lethal gene was used as positive control. Percent mortality of the nymphs on day 14 is recorded.

Example 14. Expression of an RNAi Molecule Comprising Target dsRNA in Soybean Plants This example describes introducing a construct that expresses an interfering RNA molecule into soybean cells.

14.1. Vector Construction

A binary vector is constructed that comprises at least one expression cassette designed to produce a hairpin RNA (hpRNA) of the invention. The expression cassette comprises a promoter operably linked to a sense strand of a target nucleic acid sequence, an intron that functions as a loop sequence, a corresponding antisense strand, and a terminator. The binary vector may also comprise a second cassette between the left and right T-DNA borders, designed to express a selectable marker for use in selection of transformed plant cells. The binary vector may also contain selectable markers for selection of transformed bacteria, for example transformed Agrobacterium tumefaciens bacterial cells which contain the binary vector.

14.2. Soybean Transformation

Soybean plant material can be suitably transformed and fertile plants regenerated by many methods which are known to a person skilled in the art. Fertile morphologically normal transgenic soybean plants may be obtained by: 1) production of somatic embryogenic tissue from, e.g., immature cotyledon, hypocotyl or other suitable tissue; 2) transformation by particle bombardment or infection with *Agrobacterium*; and 3) regeneration of plants. In one example, as described in U.S. Pat. No. 5,024,944, cotyledon tissue is excised from immature embryos of soybean, optionally with the embryonic axis removed, and cultured on hormone-containing medium so as to form somatic embryogenic plant material. This material is transformed using, for example, direct DNA methods, DNA coated microprojectile bombardment or infection with *Agrobacterium*, cultured on a suitable selection medium and regenerated, optionally also in the continued presence of selecting agent, into fertile transgenic soybean plants. Selection agents may be antibiotics such as kanamycin, hygromycin, or herbicides such as an HPPD inhibitor, phosphinothricin, or glyphosate or, alternatively, selection may be based upon expression of a visualisable marker gene such as GUS. Target tissues for transformation include meristematic tissue, somaclonal embryogenic tissue, and flower or flower-forming tissue. Other examples of soybean transformation include physical DNA delivery methods, such as particle bombardment (see e.g., Finer & McMullen, In Vitro Cell Dev. Biol., 1991, 27P:175-182; McCabe et al., Bio/technology, 1998, 6:923-926), whisker (Khalafalla et al., African J. of Biotechnology, 2006, 5:1594-1599), aerosol bean injection (U.S. Pat. No. 7,001,754), or by *Agrobacterium*-mediated delivery methods (Hinchee et al., Bio/Technology, 1988, 6:915-922; U.S. Pat. No. 7,002,058; U.S. Patent Application Publication Nos. 20040034889 and 20080229447; Paz et al., Plant Cell Report, 2006, 25:206-213).

Transgenic soybean plants can be generated with the above described binary vector containing an expression cassette capable of producing an interfering RNA molecule using any available transformation method. Optionally, an interfering RNA molecule expression cassette can be present in the T-DNA alongside other sequences which provide additional means of selection/identification of transformed tissue including, for example, the known genes which provide resistance to kanamycin, hygromycin, phosphinothricin, butafenacil, or glyphosate. For example, different binary vectors containing PAT or EPSPS selectable marker genes are known in the art (see e.g., U.S. Patent Application Publication No. 20080229447). Alternatively, selectable marker sequences may be present on separate polynucleotides and a process of, for example, co-transformation and co-selection is used. A scorable marker gene such as GUS may also be used to identify transformed tissue.

TO plants are taken from tissue culture to the greenhouse where they are transplanted into water-saturated soil (REDI-EARTH® Plug and Seedling Mix, Sun Gro Horticulture, Bellevue, WA, or Fafard Germinating Mix) mixed with 1% granular MARATHON® (Olympic Horticultural Products, Co., Mainland, PA) at 5-10 g/gal soil in 2" square pots. The plants are covered with humidity domes and placed in a Conviron chamber (Pembina, ND) with the following environmental conditions: 24° C. day; 20° C. night; 16-23 hours light-1-8 hours dark photoperiod; 80% relative humidity.

After plants become established in the soil and new growth appears (~1-2 weeks), plants are sampled and tested for the presence of desired transgene by TAQMAN® analysis using appropriate probes for the interfering RNA expression cassette, including, for example, for promoters, for example, prCMP. Positive plants are transplanted into 4" square pots containing Fafard #3 soil. Sierra 17-6-12 slow release fertilizer may be incorporated into the soil at the recommended rate. The plants are then relocated into a standard greenhouse to acclimate for about 1 week. The environmental conditions are: 27° C. day; 21° C. night; 14 hour photoperiod (with supplemental light); ambient humidity. After acclimation, the plants are sampled and tested in detail for the presence and copy number of inserted transgenes. Transgenic soybean plants may then be assayed for resistance to stink bug species by a feeding assay, and/or they may be grown to maturity for T1 seed production. T1 plants may be grown and may also be assayed for resistance to stink bug species by a feeding assay.

Example 15. Identification of Potential RNAi Lethal Genes in *Leptinotarsa decemlineata*

This example describes the testing of dsRNA molecules against target genes in *Leptinotarsa decemlineata* (Ld; Colorado potato beetle), that are orthologues of the *Sitophilus oryzae* target genes described in Table 1.

15.1. dsRNA Synthesis of the Candidate Target Genes in CPB

The same 96 well library synthesis platform is used to produce dsRNA samples for testing against Ld. Templates for the dsRNA molecules were produced based on publicly available transcriptome information for the Ld target genes (SEQ ID NOs:1700-1814). A negative control (dsRNA against a Green Fluorescent Protein—GFP) and a positive control (dsRNA against the species specific ubiquitin protein) are produced in the same manner.

15.2. Testing of dsRNA Samples Against Ld.

The dsRNA molecules described above are tested for toxicity against Ld larvae in laboratory bioassays. Bioassays are performed in 48-well plates using an RNA-treated artificial diet method. Briefly, molten artificial diet, is poured into each well and allowed to solidify. dsRNA molecules are diluted to the appropriate concentration. 20 μl of the dsRNA solution is added to the surface of the diet resulting in a final overlay concentration of 1 μg. One L2 larva is placed in each well and 24 larvae are tested per treatment. Plates are stored at about 25° C. with a 16 hour: 8 hour light:dark photoperiod. Mortality is recorded at 3, 4, 5, 6, 7 and 10 days post-infestation. dsRNA designed to target green fluorescent protein (GFP) is used as a negative control. dsRNA designed to the specific ubiquitin protein is used as a positive control.

It is expected that results will confirm that dsRNAs having complementarity to one or more target genes in *Leptinotarsa decemlineata* (Ld; Colorado potato beetle) (e.g., comprising any one of SEQ ID NOs:5328-5442), which are orthologues to *Sitophilus* target genes described in Table 1, are toxic to Colorado potato beetle.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

SEQUENCE LISTING

The patent contains a lengthy sequence listing. A copy of the sequence listing is available in electronic form from the USPTO web site (https://seqdata.uspto.gov/?pageRequest=docDetail&DocID=US12102091B2). An electronic copy of the sequence listing will also be available from the USPTO upon request and payment of the fee set forth in 37 CFR 1.19(b)(3).

What is claimed is:

1. An interfering ribonucleic acid (RNA) molecule wherein the interfering RNA molecule comprises at least one dsRNA having annealed complementary strands, one strand of which is complementary to a target nucleotide sequence within a pest insect target gene, and comprises SEQ ID NO: 5037, or the complement thereof; wherein the interfering RNA molecule has insecticidal activity on a hemipteran plant pest, wherein said hemipteran plant pest is *Nezara viridula*.

2. The interfering RNA molecule of claim 1, wherein the RNA comprises at least two dsRNAs, wherein each dsRNA comprises a sequence of nucleotides which is complementary to a target nucleotide sequence within the target gene.

3. The interfering RNA molecule of claim 2, wherein each of the dsRNAs comprise a different sequence of nucleotides which is complementary to a different target nucleotide sequence within the target gene.

4. The interfering RNA molecule of claim 1, wherein the dsRNA is a region of double-stranded RNA comprising fully complementary annealed strands.

5. A nucleic acid construct comprising the interfering RNA molecule claim 1.

6. A nucleic acid molecule encoding the interfering RNA molecule of claim 1.

7. A nucleic acid construct comprising a nucleotide sequence that encodes the nucleic acid molecule of claim 6.

8. The nucleic acid construct of claim 5, wherein the nucleic acid construct is an expression vector.

9. A recombinant vector comprising a regulatory sequence operably linked to a nucleotide sequence that encodes the interfering RNA molecule of claim 1.

10. An insecticidal composition for inhibiting the expression of a *Nezara viridula* insect target gene, comprising the interfering RNA of claim 1 and an agriculturally acceptable carrier.

* * * * *